US008088887B2

(12) United States Patent
Wu et al.

(10) Patent No.: US 8,088,887 B2
(45) Date of Patent: Jan. 3, 2012

(54) PEPTIDE-CONJUGATES THAT BIND TO VEGF-STIMULATED OR TUMOR VASCULATURE AND METHODS OF TREATMENT

(75) Inventors: Han-Chung Wu, Taipei (TW); Chin-Tarng Lin, Taipei (TW); Tong-Young Lee, Taipei (TW); Szu-Yao Kuo, Taipei (TW)

(73) Assignees: Academia Sinica, Taipei (TW); National Taiwan University, Taipei (TW)

( * ) Notice: Subject to any disclaimer, the term of this patent is extended or adjusted under 35 U.S.C. 154(b) by 723 days.

(21) Appl. No.: 11/783,926

(22) Filed: Apr. 13, 2007

(65) Prior Publication Data

US 2008/0193510 A1  Aug. 14, 2008

Related U.S. Application Data

(60) Provisional application No. 60/900,980, filed on Feb. 13, 2007, provisional application No. 60/901,086, filed on Feb. 14, 2007.

(51) Int. Cl.
*A61K 38/00* (2006.01)
*A61K 38/18* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)
*C07K 14/515* (2006.01)
*A61P 35/00* (2006.01)

(52) U.S. Cl. .................. 530/300; 514/8.1; 514/13.3
(58) Field of Classification Search .................. None
See application file for complete search history.

(56) References Cited

U.S. PATENT DOCUMENTS

| 4,179,337 A | 12/1979 | Davis |
| 4,301,144 A | 11/1981 | Iwashita |
| 4,496,689 A | 1/1985 | Mitra |
| 4,640,835 A | 2/1987 | Shimizu |
| 4,670,417 A | 6/1987 | Iwasaki |
| 4,791,192 A | 12/1988 | Nakagawa |
| 5,283,317 A | 2/1994 | Saifer |
| 6,051,251 A | 4/2000 | Zalipsky |
| 6,355,267 B1 | 3/2002 | Collins |
| 6,498,027 B1 * | 12/2002 | Van Es et al. ............ 435/235.1 |
| 6,663,885 B1 | 12/2003 | Hager |
| 6,974,884 B2 | 12/2005 | Rains |

FOREIGN PATENT DOCUMENTS

| EP | 0960942 A2 | 12/1999 |
| EP | 1537858 A1 | 6/2005 |
| WO | WO 95/34326 | 12/1995 |
| WO | WO03037172 | * 5/2003 |

OTHER PUBLICATIONS

Partial International Search Report, mailed Apr. 1, 2009, in related International application No. PCT/US2008/084043.
Han et al: "Pathogenomic sequence analysis of Bacillus cereus and Bacillus thuringiensis isolates closely related to Bacillus anthracis" Journal of Bacteriology, American Society for Microbiology, US, vol. 188, No. 9, May 1, 2006, pp. 3382-3390.
Du et al: "In vitro panning of a targeting peptide to hepatocarcinoma from a phage display peptide library" Biochemical and Biophysical Research Communications, Academic Press Inc. Orlando, FL, US, vol. 342, No. 3, Apr. 14, 2006, pp. 956-962.
Allen: "Ligand-targeted therapeutics in anticancer therapy" Nature Reviews. Cancer, Natur Publishing Group, London, GB, vol. 2, No. 10, Oct. 1, 2002, pp. 750-763.
Krumpe et al: "The Use of Phase-Displayed Peptide Libraries to Develop Tumor-Targeting Drugs" International Journal of Peptide Research and Therapeutics; Formerly Known as Ketters in Peptide Science, Kluwer Academic Publishers, DO, vol. 12, No. 1, Mar. 1, 2006, pp. 79-91.
Halm et al: "A phase II study of pegylated liposomal doxorubicin for treatment of advanced hepatocellular carcinoma." Annals of Oncology: Official Journal of the European Society for Medical Oncology / ESMO Jan. 2000, vol. 11, No. 1, Jan. 2000, pp. 113-114.
USP pharmaceutical excipients listing. USP and NF Excipients, p. 2404-2406, USP 24 NF 19, United States Pharmacopeial Convention Inc., Rockville, Md. (ISBN 1-889788-03-1) (1999).
Kuo Szu-Yao, "Identification of Oral Cancer-Targeted Peptides by in vivo Phage Display and Development of Ligand-Targeted Therapy for Oral Cancer," Graduate Thesis No. R91450011, indexed and shelved at the National Taiwanese University Library on Sep. 30, 2004, Of Chinese-language portions.
Lee Tong-Young, "Development of the Novel Tumor-Homing Peptides for Drug Delivery and Application in Chemotherapy," Graduate Thesis No. D88444001, indexed and shelved at the National Taiwanese University Library on Mar. 17, 2005, Of Chinese-language portions.
International Search Report and Witten Opinion in PCT/US2008/001810.
Allen T M et al. (2002) Adventures in Targeting. Journal of Liposome Research, Taylor & Francis, Philadelphia, PA, US, vol. 12, No. 1/02, Jan. 1, 2002, pp. 5-12, XP001126048.
Allen, T. M., and Chonn, A. (1987). Large unilamellar liposomes with low uptake into the reticuloendothelial system. FEBS letters 223, 42-46.

(Continued)

*Primary Examiner* — Robert Landsman
(74) *Attorney, Agent, or Firm* — Finnegan, Henderson, Farabow, Garrett & Dunner, LLP

(57) ABSTRACT

The invention provides nucleic acids, peptides, and antibodies for use in applications including diagnosis and therapy. The peptides target neovasculature and were identified by in vivo phage display. One such peptide, SP5-52, recognized the neovasculature of multiple tumors in SCID mice, but did not target normal blood vessels. This peptide also binds to blood vessels of human lung cancer biopsy specimens. Liposomes comprising SP5-52 and doxorubicin enhanced the efficacy of the drug against multiple human cancer xenografts in SCID mice.

22 Claims, 7 Drawing Sheets

OTHER PUBLICATIONS

Allen, T. M. et al. (1991). Liposomes containing synthetic lipid derivatives of poly(ethylene glycol) show prolonged circulation half-lives in vivo. Biochimica et biophysica acta 1066, 29-36.

Blume, G., and Cevc, G. (1990). Liposomes for the sustained drug release in vivo. Biochimica et biophysica acta 1029, 91-97.

Gabizon, A., and Papahadjopoulos, D. (1988). Liposome formulations with prolonged circulation time in blood and enhanced uptake by tumors. Proc Natl Acad Sci U.S.A. 85, 6949-6953.

Grant, G. (1992) Synthetic Peptides, A Users Guide, W.H. Freeman and Co. Chapter 3.

Gregoriadis, G. et al. (1974). Drug-carrier potential of liposomes in cancer chemotherapy. Lancet 1, 1313-1316.

Hermanson, G.T. (1996) Bioconjugate Techniques; Academic Press. Chapters 3 and 9.

Klibanov, A. L. et al. (1990). Amphipathic polyethyleneglycols effectively prolong the circulation time of liposomes. FEBS letters 268, 235-237.

Lee Tong-Young et al. (2007) Peptide-mediated targeting to tumor blood vessels of lung cancer for drug delivery. Cancer Research, vol. 67, No. 22, Nov. 2007, pp. 10958-10965, XP002488417.

Maeda N et al. (2004) Synthesis of angiogenesis-targeted peptide and hydrophobized polyethylene glycol conjugate. Bioorganic & Medicinal chemistry Letters, Oxford, GB, vol. 14, No. 4, Feb. 23, 2004, pp. 1015-1017, XP002411827.

Moreira J N et al. (2004) Antagonist G-mediated targeting and cytotoxicity of liposomal doxorubicin in CL1-H82 variant small cell lung cancer. Brazilian Journal of Medical and Biological Research, vol. 37, No. 8, Aug. 2004, pp. 1185-1192, XP002488418.

Moreira J N et al. (2001) A growth factor antagonist as a targeting agent for sterically stabilized liposomes in human small cell lung cancer. Biochimica Et Biophysica Acta. Biomembranes, Amsterdam, NL, vol. 1514, No. 2, Oct. 1, 2001, pp. 303-317, XP004319634.

Pastorino, F. et al. (2006) Targeting liposomal chemotherapy via both tumor cell-specific and tumor vasculature-specific ligands potentiates therapeutic efficacy. Cancer Research, vol. 66, No. 20, Oct. 2006, pp. 10073-10082, XP002488419.

Senior, J. H. (1987). Fate and behavior of liposomes in vivo: a review of controlling factors. Critical reviews in therapeutic drug carrier systems 3, 123-193.

Senior, J. et al. (1991). Influence of surface hydrophilicity of liposomes on their interaction with plasma protein and clearance from the circulation: studies with poly(ethylene glycol)-coated vesicles. Biochimica et biophysica acta 1062, 77-82.

Sugano M et al. (2000) Antibody targeting of doxorubicin-loaded liposomes suppresses the growth and metastatic spread of established human lung tumor xenografts in severe combined immunodeficient mice. Cancer Research, American Association for Cancer Research, Baltimore, MD, vol. 60, No. 24, Dec. 15, 2000, pp. 6942-6949, XP000980029.

Weinstein, J. N. (1984). Liposomes as drug carriers in cancer therapy. Cancer treatment reports 68, 127-135.

Woodle, M. C., and Lasic, D. D. (1992). Sterically stabilized liposomes. Biochimica et biophysica acta 1113, 171-199.

Wu, N. Z. et al. (1993). Increased microvascular permeability contributes to preferential accumulation of Stealth liposomes in tumor tissue. Cancer research 53, 3765-3770.

Afsa., H. (1966). Determination of free amino groups in protein by trinitrobenzene sulfuric acid. Anal Biochem 14, 328.

Arap, W., Pasqualini, R., and Ruoslahti, E. (1998). Cancer treatment by targeted drug delivery to tumor vasculature in a mouse model. Science 279, 377-380.

Atwell, S., Ultsch, M., De Vos, A. M., and Wells, J. A. (1997). Structural plasticity in a remodeled protein-protein interface. Science 278, 1125-1128.

Barry, M. A., Dower, W. J., and Johnston, S. A. (1996). Toward cell-targeting gene therapy vectors: selection of cell-binding peptides from random peptide-presenting phage libraries. Nat Med 2, 299-305.

Bartel P, Chien CT, Sternglanz R, Fields S. (1993). Elimination of false positives that arise in using the two-hybrid system. Biotechniques 14:920-924.

Bergers, G., Song, S., Meyer-Morse, N., Bergsland, E., and Hanahan, D. (2003). Benefits of targeting both pericytes and endothelial cells in the tumor vasculature with kinase inhibitors. The Journal of clinical investigation 111, 1287-1295.

Boehm, T., Folkman, J., Browder, T., and O'Reilly, M. S. (1997). Antiangiogenic therapy of experimental cancer does not induce acquired drug resistance. Nature 390, 404-407.

Bottger, V., Bottger, A., Howard, S. F., Picksley, S. M., Chene, P., Garcia-Echeverria, C., Hochkeppel, H. K., and Lane, D. P. (1996). Identification of novel mdm2 binding peptides by phage display. Oncogene 13, 2141-2147.

Boucher, Y., Baxter, L. T., and Jain, R. K. (1990). Interstitial pressure gradients in tissue-isolated and subcutaneous tumors: implications for therapy. Cancer research 50, 4478-4484.

Boucher, Y., Kirkwood, J. M., Opacic, D., Desantis, M., and Jain, R. K. (1991). Interstitial hypertension in superficial metastatic melanomas in humans. Cancer research 51, 6691-6694.

Burrows, F. J., and Thorpe., P. E. (1994). Vascular targeting: A new approach to the therapy of solid tumors. Pharmacol Ther 64, 155-174.

Castano, A. R., Tangri, S., Miller, J. E., Holcombe, H. R., Jackson, M. R., Huse, W. D., Kronenberg, M., and Peterson, P. A. (1995). Peptide binding and presentation by mouse CD1. Science 269, 223-226.

Chu, Y. W., Yang, P. C., Yang, S. C., Shyu, Y. C., Hendrix, M. J., Wu, R., and Wu, C. W. (1997). Selection of invasive and metastatic subpopulations from a human lung adenocarcinoma cell line. American journal of respiratory cell and molecular biology 17, 353-360.

De Vita F, Orditura M, Infusino S, Martinelli E, Merola MC, Morgillo F, Cosenza A, Di Martino N, Del Genio A, Catalano G. (2001). Preoperative chemo-radiotherapy for carcinoma of the esophagus. Tumori. 87, S24-7.

DeLeo, F. R., Yu, L., Burritt, J. B., Loetterle, L. R., Bond, C. W., Jesaitis, A. J., and Quinn, M. T. (1995). Mapping sites of interaction of p47-phox and flavocytochrome b with random-sequence peptide phage display libraries. Proc Natl Acad Sci U S A 92, 7110-7114.

Denekamp, J. (1993). Angiogenesis, neovascular proliferation and vascular pathophysiology as targets for cancer therapy. Br J Radiol 66, 181-196.

D'Mello, F., Partidos, C. D., Steward, M. W., and Howard, C. R. (1997). Definition of the primary structure of hepatitis B virus (HBV) pre-S hepatocyte binding domain using random peptide libraries. Virology 237, 319-326.

Drummond, D. C., Meyer, O., Hong, K., Kirpotin, D. B., and Papahadjopoulos, D. (1999). Optimizing liposomes for delivery of chemotherapeutic agents to solid tumors. Pharmacological reviews 51, 691-743.

Dvorak, H. F., Nagy, J. A., and Dvorak, A. M. (1991). Structure of solid tumors and their vasculature: implications for therapy with monoclonal antibodies. Cancer Cells 3, 77-85.

Eliceiri, B. P., and Cheresh, D. A. (1999). The role of alphav integrins during angiogenesis: insights into potential mechanisms of action and clinical development. The Journal of clinical investigation 103, 1227-1230.

Essler, M., and Ruoslahti, E. (2002). Molecular specialization of breast vasculature: a breast-homing phage-displayed peptide binds to aminopeptidase P in breast vasculature. Proc Natl Acad Sci U S A 99, 2252-2257.

Folgori, A., Tafi, R., Meola, A., Felici, F., Galfre, G., Cortese, R., Monaci, P., and Nicosia, A. (1994). A general strategy to identify mimotopes of pathological antigens using only random peptide libraries and human sera. Embo J 13, 2236-2243.

Fu, Y., Shearing, L. N., Haynes, S., Crewther, P., Tilley, L., Anders, R. F., and Foley, M. (1997). Isolation from phage display libraries of single chain variable fragment antibodies that recognize conformational epitopes in the malaria vaccine candidate, apical membrane antigen-1. J Biol Chem 272, 25678-25684.

Gabizon, A., and Martin, F. (1997). Polyethylene glycol-coated (pegylated) liposomal doxorubicin. Rationale for use in solid tumours. Drugs 54 Suppl 4, 15-21.

Grant, G. (1992) Synthetic Peptides, A Users Guide, W.H. Freeman and Co.

Gutmann, R., Leunig, M., Feyh, J., Goetz, A. E., Messmer, K., Kastenbauer, E., and Jain, R. K. (1992). Interstitial hypertension in head and neck tumors in patients: correlation with tumor size. Cancer research 52, 1993-1995.

Heldin, C. H., Rubin, K., Pietras, K., and Ostman, A. (2004). High interstitial fluid pressure—an obstacle in cancer therapy. Nature reviews 4, 806-813.
Hermanson, G.T. (1996) Bioconjugate Techniques; Academic Press.
Hoffman, J. A., Giraudo, E., Singh, M., Zhang, L., Inoue, M., Porkka, K., Hanahan, D., and Ruoslahti, E. (2003). Progressive vascular changes in a transgenic mouse model of squamous cell carcinoma. Cancer cell 4, 383-391.
Hug, P., and Sleight R.G. (1991). Liposomes for the transformation of eukaryotic cells. Biochim Biophys Acta. 1097, 1-17.
Hunkapiller et al., (1984) A microchemical facility for the analysis and synthesis of genes and proteins Nature, 310, 105-111.
Iwabuchi K, Li B, Bartel P, and Fields S. (1993). Use of the two-hybrid system to identify the domain of p53 involved in oligomerization. Oncogene 8:1693-1696.
Kirpotin, D., Park, J. W., Hong, K., Zalipsky, S., Li, W. L., Carter, P., Benz, C. C., and Papahadjopoulos, D. (1997). Sterically stabilized anti-HER2 immunoliposomes: design and targeting to human breast cancer cells in vitro. Biochemistry 36, 66-75.
Koivunen, E., Arap, W., Rajotte, D., Landenranta, J., and Pasqualini, R. (1999). Identification of receptor ligands with phage display peptide libraries. J Nucl Med 40, 883-888.
Kraft, S., Diefenbach, B., Mehta, R., Jonczyk, A., Luckenbach, G. A., and Goodman, S. L. (1999). Definition of an unexpected ligand recognition motif for alphav beta6 integrin. J Biol Chem 274, 1979-1985.
Kreitman and Pastan, Immunotoxins in the treatment of hematologic malignancies. Curr Drug Targets. 7, 1301-11 (2006).
Lasic DD, Ceh B, Stuart MC, Guo L, Frederik PM, Barenholz Y. (1995). Transmembrane gradient driven phase transitions within vesicles: lessons for drug delivery. Biochim Biophys Acta. 1239, 145-56.
Lee, T. Y., Wu, H. C., Tseng, Y. L., and Lin, C. T. (2004). A novel peptide specifically binding to nasopharyngeal carcinoma for targeted drug delivery. Cancer Res 64, 8002-8008.
Less, J. R., Posner, M. C., Boucher, Y., Borochovitz, D., Wolmark, N., and Jain, R. K. (1992). Interstitial hypertension in human breast and colorectal tumors. Cancer research 52, 6371-6374.
Li, B., Tom, J. Y., Oare, D., Yen, R., Fairbrother, W. J., Wells, J. A., and Cunningham, B. C. (1995). Minimization of a polypeptide hormone. Science 270, 1657-1660.
Lichtenberg D., and Barenholz, Y. (1988). Methods of Biochemical Analysis, vol. 33, 337-462.
Liu, I. J., Hsueh, P. R., Lin, C. T., Chiu, C. Y., Kao, C. L., Liao, M. Y., and Wu, H. C. (2004). Disease-specific B Cell epitopes for serum antibodies from patients with severe acute respiratory syndrome (SARS) and serologic detection of SARS antibodies by epitope-based peptide antigens. J Infect Dis 190, 797-809.
Madura, K., Dohmen, R.J., and Varshavsky, A. (1993) N-recognin/Ubc2 interactions in the N-end rule pathway. J. Biol. Chem. 268:12046-12054.
Martin, F. J. (1998). Clinical pharmacology and antitumor efficacy of DOXIL (pegylated liposomal doxorubicin), in Medical Applications of Liposomes (Lasic DD and Papahadjopoulos D eds), (New York: Elsevier Science BV).
Mazzucchelli, L, Burritt, J. B., Jesaitis, A. J., Nusrat, A., Liang, T. W., Gewirtz, A. T., Schnell, F. J., and Parkos, C. A. (1999). Cell-specific peptide binding by human neutrophils. Blood 93, 1738-1748.
Monfardini, C., et al. (1995) A branched monomethoxypoly(ethylene glycol) for protein modification. Bioconjugate Chem. 6, 62-69.
Ng EW, Shima DT, Calias P, Cunningham ET Jr, Guyer DR, Adamis AP (2006) Pegaptanib, a targeted anti-VEGF aptamer for ocular vascular disease. Nat Rev Drug Discov. 5, 123-32.
Nord, K., Gunneriusson, E., Ringdahl, J., Stahl, S., Uhlen, M., and Nygren, P. A. (1997). Binding proteins selected from combinatorial libraries of an alpha-helical bacterial receptor domain. Nat Biotechnol 15, 772-777.
Oku, N., Asai, T., Watanabe, K., Kuromi, K., Nagatsuka, M., Kurohane, K., Kikkawa, H., Ogino, K., Tanaka, M., Ishikawa, D., et al. (2002). Anti-neovascular therapy using novel peptides homing to angiogenic vessels. Oncogene 21, 2662-2669.
Papahadjopoulos, D., Allen, T. M., Gabizon, A., Mayhew, E., Matthay, K., Huang, S. K., Lee, K. D., Woodle, M. C., Lasic, D. D., Redemann, C., and et al. (1991). Sterically stabilized liposomes: improvements in pharmacokinetics and antitumor therapeutic efficacy. Proc Natl Acad Sci U.S.A. 88, 11460-11464.
Park, J. W., Hong, K., Kirpotin, D. B., Colbern, G., Shalaby, R., Baselga, J., Shao, Y., Nielsen, U. B., Marks, J. D., Moore, D., et al. (2002). Anti-HER2 immunoliposomes: enhanced efficacy attributable to targeted delivery. Clin Cancer Res 8, 1172-1181.
Pasqualini, R., and Ruoslahti, E. (1996). Organ targeting in vivo using phage display peptide libraries. Nature 380, 364-366.
Pasqualini, R., Koivunen, E., and Ruoslahti, E. (1995). A peptide isolated from phage display libraries is a structural and functional mimic of an RGD-binding site on integrins. J Cell Biol 130, 1189-1196.
Pasqualini, R., Koivunen, E., and Ruoslahti, E. (1997). Alpha v integrins as receptors for tumor targeting by circulating ligands. Nature biotechnology 15, 542-546.
Prezzi, C., Nuzzo, M., Meola, A., Delmastro, P., Galfre, G., Cortese, R., Nicosia, A., and Monaci, P. (1996). Selection of antigenic and immunogenic mimics of hepatitis C virus using sera from patients. J Immunol 156, 4504-4513.
Ruoslahti, E. (2002). Specialization of tumour vasculature. Nature reviews 2, 83-90.
Scott, J. K., and Smith, G. P. (1990). Searching for peptide ligands with an epitope library. Science 249, 386-390.
Shockley, T. R., Lin, K., Nagy, J. A., Tompkins, R. G., Dvorak, H. F., and Yarmush, M. L. (1991). Penetration of tumor tissue by antibodies and other immunoproteins. Annals of the New York Academy of Sciences 618, 367-382.
Smith, W. C., McDowell, J. H., Dugger, D. R., Miller, R., Arendt, A., Popp, M. P., and Hargrave, P. A. (1999). Identification of regions of arrestin that bind to rhodopsin. Biochemistry 38, 2752-2761.
Speth, P. A., van Hoesel, Q. G., and Haanen, C. (1988). Clinical pharmacokinetics of doxorubicin. Clinical pharmacokinetics 15, 15-31.
Stefano et al. (2006) A conjugate of doxorubicin with lactosaminated albumin enhances the drug concentrations in all the forms of rat hepatocellular carcinomas independently of their differentiation grade. Liver Int. 26, 726-33.
Suter, B., Auerbach, D., and Stagljar, I.(2006). Yeast-based functional genomics and proteomics technologies: the first 15 years and beyond. Biotechniques 40:625-44.
Tseng YL, Hong RL, Tao MH, Chang FH. (1999). Sterically stabilized anti-idiotype immunoliposomes improve the therapeutic efficacy of doxorubicin in a murine B-cell lymphoma model. Int J Cancer. 80:723-30.
Tseng, Y. L., Hong, R. L., Tao, M. H., and Chang, F. H. (1999). Sterically stabilized anti-idiotype immunoliposomes improve the therapeutic efficacy of doxorubicin in a murine B-cell lymphoma model. International journal of cancer 80, 723-730.
Wrighton, N. C., Farrell, F. X., Chang, R., Kashyap, A. K., Barbone, F. P., Mulcahy, L. S., Johnson, D. L., Barrett, R. W., Jolliffe, L. K., and Dower, W. J. (1996). Small peptides as potent mimetics of the protein hormone erythropoietin. Science 273, 458-464.
Wu, H. C., Huang, Y. L., Chao, T. T., Jan, J. T., Huang, J. L., Chiang, H. Y., King, C. C., and Shaio, M. F. (2001). Identification of B-cell epitope of dengue virus type 1 and its application in diagnosis of patients. J Clin Microbiol 39, 977-982.
Wu, H. C., Jung, M. Y., Chiu, C. Y., Chao, T. T., Lai, S. C., Jan, J. T., and Shaio, M. F. (2003). Identification of a dengue virus type 2 (DEN-2) serotype-specific B-cell epitope and detection of DEN-2-immunized animal serum samples using an epitope-based peptide antigen. J Gen Virol 84, 2771-2779.
Zalipsky, S. (1995) Functionalized poly(ethylene glycol) for preparation of biologically relevant conjugates. Bioconjugate Chem., 6:150-165.
Zalipsky, S., Mullah, N., Harding, J. A., Gittelman, J., Guo, L., and DeFrees, S. A. (1997). Poly(ethylene glycol)-grafted liposomes with oligopeptide or oligosaccharide ligands appended to the termini of the polymer chains. Bioconjugate chemistry 8, 111-118.
Zervos A.S., Gyuris, J., and Brent, R. (1993). Mxi1, a protein that specifically interacts with Max to bind Myo-Max recognition sites. Cell. 72(2):223-32.

* cited by examiner

SEQUENCE LISTING

```
<160> NUMBER OF SEQ ID NOS: 20

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tctgtttctg tgggtatgaa gccgagtcct aggcct                              36

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Val Ser Val Gly Met Lys Pro Ser Pro Arg Pro
 1               5                  10

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 3
tggccgctgc atacttctgt ttatcctcct tctccg          36

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Pro Leu His Thr Ser Val Tyr Pro Pro Ser Pro
 1               5                  10

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aatactttgc cgccgttttc tccgccgtcg ccgcct          36

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Thr Leu Pro Pro Phe Ser Pro Pro Ser Pro Pro
 1               5                  10

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcgtttcctg atagtaatat tgctccgagt agtcct          36

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Phe Pro Asp Ser Asn Ile Ala Pro Ser Ser Pro
 1               5                  10

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 9
cagcatgctc cttctaattc gaagtctgtt cttact					36

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln His Ala Pro Ser Asn Ser Lys Ser Val Leu Thr
 1               5                  10

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gttaattcgc attaggctct gtggagtcct gctcag					36

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Asn Ser His Gln Ala Leu Trp Ser Pro Ala Gln
 1               5                  10

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tctcctatgt ttactatgat tcaaggtgat gctcaa					36

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Pro Met Phe Thr Met Ile Gln Gly Asp Ala Gln
 1               5                  10

<210> SEQ ID NO 15
<211> LENGTH: 35
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 15
ctcctcttct ttctactcgt gctgttcaac tttct                                     35

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Pro Leu Leu Ser Thr Arg Ala Val Gln Leu Ser
 1               5                  10

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tctactttgc ctccgcctct gcgttttgct aatgtg                                    36

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Thr Leu Pro Pro Pro Leu Arg Phe Ala Asn Val
 1               5                  10

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccctcatagt tagcgtaacg                                                      20

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Val Ser Val Gly Met Lys Gly Gly Gly Arg Pro
 1               5                  10
```

PEPTIDE-CONJUGATES THAT BIND TO VEGF-STIMULATED OR TUMOR VASCULATURE AND METHODS OF TREATMENT

PRIORITY CLAIM

This application claims priority to provisional applications 60/900,980, filed Feb. 13, 2007, and 60/901,086, filed Feb. 14, 2007, which are incorporated by reference in their entirety.

BACKGROUND OF THE INVENTION

During tumor progression, tumor cells require more oxygen and metabolites to remove waste products. In addition gaining access to the host vascular system and generation of a tumor blood supply are rate-limiting steps for tumor progression (Bergers et al., 2003). Similarly, diseases such as age-related macular degeneration are accompanied the generation of new blood vessels. (Ng et al., 2006). Thus, tumor blood vessels are prime targets for inhibiting tumor growth and the blood vessels that accompany age-related macular degeneration are suitable targets for inhibiting this disease. Tumor blood vessels express specific markers that are not present in the blood vessels of normal tissues. Many of these specific markers are proteins associated with tumor-induced angiogenesis, the sprouting of new blood vessels (Ruoslahti, 2002). The cell adhesion receptors, integrins $\alpha_v\beta_3$ and $\alpha_v\beta_5$, are over-expressed in tumor vasculature (Eliceiri and Cheresh, 1999). Indeed, one of the RGD-peptides identified by in vivo phage-display for tumor homing, or targeting, recognizes $\alpha_v\beta_5$ (Pasqualini et al., 1997). Peptides specific for these integrins have been used as ligands for targeted delivery of anti-cancer and anti-angiogenic agents (Arap et al., 1998). The heterogeneity in the vasculature might provide new opportunities for targeted delivery of therapies.

Conventional chemotherapy is limited by its toxicity to normal tissues. Therapeutic results might be greatly improved if the chemotherapeutic drugs could bind directly to tumor sites or tumor vessels and be kept away from normal tissues. Most small-molecule chemotherapeutic agents have a large volume of distribution on intravenous (i.v.) administration (Speth et al., 1988). This distribution often leads to a narrow therapeutic index due to a high level of toxicity to normal tissues. Through encapsulation of drugs in a macromolecular carrier, such as liposomes, the volume of distribution is significantly reduced and the concentration of drug in the tumor is increased (Drummond et al., 1999). Encapsulation can decrease the severity and types of nonspecific toxicities and can increase in the amount of drug that is effectively delivered to the tumor site (Gabizon and Martin, 1997; Martin, 1998; Papahadjopoulos et al., 1991). A tumor targeting ligand can be used to target macromolecular carriers, such as liposomes, to the tumor site. Alternatively, drugs can be conjugated or linked to the tumor targeting ligand to facilitate targeting of the drug to the tumor.

Liposomes were suggested as drug carriers in cancer chemotherapy (Gregoriadis et al., 1974). Since then, interest in liposomes has increased and liposome systems are now being extensively studied as drug carriers. Three basic requirements are desired for liposomes for use in specifically delivering drugs: (i) prolonged blood circulation, (ii) sufficient accumulation in tumors or other target tissues, (iii) controlled drug release and uptake by tumor cells or other target tissues with a release profile matching the pharmacodynamics of the drug.

Initially, the research in liposome drug delivery systems suffered from very fast blood clearance by the reticuloendothelial system (RES). It was recognized that particle size, surface charge (Weinstein, 1984), and liposome composition strongly influenced the clearance profile (e.g., incorporation of phosphatidylinositols or monosialogangliosides prolongs liposome circulation in the blood) (Allen and Chonn, 1987; Gabizon and Papahadjopoulos, 1988; Senior, 1987). This uptake may be evaded by 'stealth' liposomes, which preferentially exit the circulation via leaky capillaries and are predicted to accumulate in tumors or other diseased tissue exhibiting extensive neo-vascularisation leading to higher concentrations and enhanced efficacy (Wu et al., 1993).

However, liposomes were only fully recognized as successful drug delivery candidates when it was discovered that liposomes coated with the synthetic polymer polyethyleneglycol (PEG) had significantly increased half-life in the blood (Allen et al., 1991; Blume and Cevc, 1990; Klibanov et al., 1990; Papahadjopoulos et al., 1991; Senior et al., 1991). The pegylated liposomes are long circulating due to a highly hydrated and protected liposome surface, which inhibits protein adsorption and opsonization of the liposomes (Woodle and Lasic, 1992). Having solved the problems of fast opsonization and clearance, providing liposomes with up to 72 h half-life in the blood (Drummond et al., 1999), the next challenge was to get the liposomes to accumulate in the tumor tissue or other diseased tissues through active targeting.

The use of targeting liposomes can potentially lead to significantly enhanced drug release at tumor target sites and increased therapeutic efficacy (Lee et al. 2004; Park et al 2002). The drug delivery research field has successfully constructed long circulating liposomes that accumulate in tumor tissue where the entrapped drugs then leak out of the liposomes by passive diffusion, unless there is an active trigger present. The use of site-specific triggers that can release drugs specifically in diseased tissue is one way of increasing drug bioavailability at the tumor target site. Another way of optimizing drug bioavailability is to obtain a higher degree of liposome accumulation by active targeting. Furthermore, the combination of active targeting with active triggering can potentially lead to significantly enhanced and specific drug release at the tumor target site (Lee et al., 2004; Park et al., 2002).

For solid malignancies, which comprise more than 90% of human cancers, antibodies recognizing tumor-specific antigens have provided little utility for drug delivery since immunoconjugates cannot penetrate tumor tissue (Dvorak et al., 1991; Shockley et al., 1991). However, the development of phage-displayed peptide libraries over the past decade has ushered in the opportunity to identify small peptides that are more effective than antibodies.

Phage-displayed random peptide libraries provide opportunities to map B-cell epitopes (D'Mello et al., 1997; Fu et al., 1997; Scott and Smith, 1990; Wu et al., 2001; Wu et al., 2003) and protein-protein contacts (Atwell et al., 1997; Bottger et al., 1996; Nord et al., 1997; Smith et al., 1999), select bioactive peptides bound to receptors (Koivunen et al., 1999; Li et al., 1995; Wrighton et al., 1996) or proteins (Bottger et al., 1996; Castano et al., 1995; DeLeo et al., 1995; Kraft et al., 1999; Pasqualini et al., 1995), search for disease-specific antigen mimics (Folgori et al., 1994; Liu et al., 2004; Prezzi et al., 1996), and determine cell-specific (Barry et al., 1996; Lee et al., 2004; Mazzucchelli et al., 1999) and organ-specific peptides (Arap et al., 1998; Essler and Ruoslahti, 2002; Pasqualini et al., 1995; Pasqualini and Ruoslahti, 1996).

Screening phage display libraries against specific target tissues would therefore be a direct and fast method in identifying peptide sequences, which are used for targeting of drug or gene delivery vectors. The invention discloses peptides identified by phage display that have therapeutic and diagnostic applications.

SUMMARY OF THE INVENTION

The present invention, inter alia, comprises the following, alone or in combination:

The invention provides polynucleotides, and variants thereof, including SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17.

The invention provides peptides, and variants thereof, including SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18. In one embodiment, the peptide is SEQ ID NO: 2 or a variant thereof. In another embodiment, the peptide is SEQ ID NO: 2. In another embodiment, the peptides comprise fusion proteins. In another embodiment, the peptides comprise one or more labels. In another embodiment, the peptides are conjugated to one or more drugs. Drugs that may be conjugated to the peptides include doxorubicin, vinorelbine, an oligonucleotide, a toxin, an anti-VEGF aptamer, and a radioactive molecule.

The invention provides antibodies that bind to the peptides of the invention, or variants thereof, selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

The invention provides liposomes comprising at least one peptide selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18. In one embodiment, the liposome comprises SEQ ID NO: 2, or a variant thereof. In another embodiment, the liposome comprises SEQ ID NO: 2. The liposomes may comprise one or more drugs selected from the group consisting of doxorubicin, vinorelbine, an oligonucleotide, a toxin, an anti-VEGF aptamer, and a radioactive molecule. One of the drugs that may be used is doxorubicin, which can be in an amount from about 110 μg to about 130 μg per timol phospholipid. In an embodiment, the liposomes have diameters from about 65 nm to about 75 nm. In another embodiment, the number of peptide molecules per liposome is from about 300 to about 500. The liposomes may comprise a pharmaceutically acceptable carrier.

The invention provides methods of treating diseases comprising administering a peptide of the invention to a subject in need of treatment wherein said peptide is conjugated to a drug. Drugs that may be conjugated to the peptide include doxorubicin, vinorelbine, an oligonucleotide, a toxin, an anti-VEGF aptamer, and a radioactive molecule.

The invention provides methods of treating diseases comprising contacting a subject with a liposome comprising one or more drugs, and more or more peptides, or variants thereof, selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18. The method may comprise contacting a subject with a liposome comprising one or more drugs and SEQ ID NO: 2, or a variant thereof. The liposome may comprise one or more chemotherapeutic drugs. The therapeutic drug may be doxorubicin. The method may be used to treat cancer, which may include a cancer selected from the group consisting of lung cancer, colon cancer, breast cancer, prostate cancer, liver cancer, pancreatic cancer, and oral cancer. In one embodiment, the cancer is lung cancer. In another embodiment, the cancer is oral cancer. The method may be used to treat age-related macular degeneration.

The invention provides methods of detecting neovasculature comprising contacting a specimen with a peptide of the invention under conditions that allow binding of the peptide to neovasculature, and detecting the peptide. The peptide may be detected with an antibody to the peptide. The peptide may comprise a fusion protein comprising an eptitope, and the fusion protein is detected with an antibody to the epitope. The peptide may comprise a label, and the peptide is detected by detecting the label of the peptide. In one embodiment, the label comprises FITC. In another embodiment, the label comprises biotin.

The invention provides a method of identifying a biological molecule that binds to the peptide of the invention, contacting a cellular extract with the peptide of the invention under conditions that allow formation of a complex comprising the peptide and the ligand, and analyzing the complex to identify the ligand.

The invention provides a polynucleotide that hybridizes to the complement of the polynucleotide of claim 1 under stringent conditions.

The invention provides a vector comprising the polynucleotide of claim 1, and a host cell comprising the vector.

The invention provides peptides encoded by a polynucleotide that hybridizes to the complement of the polynucleotide of claim 1 under stringent conditions.

BRIEF DESCRIPTION OF THE FIGURES AND TABLE

BRIEF DESCRIPTION OF THE TABLE

Table 1 provides phage-displayed peptide sequences from phage selected from lung cancer xenografts.

DETAILED DESCRIPTION OF THE INVENTION

Most cancer chemotherapy is accompanied by strong side effects and acquired drug resistance. Therefore, there is a need in the art for drug delivery systems that deliver the drugs to the target site not only on tumor vessels but also on tumor cells. Some attempts include the use of single-chain Fv (scFv) antibodies (Park et al., 2002) and targeting peptides (Lee et al., 2004) against tumor tissues. Recently, vascular targeting has become a focus of interest, since certain drugs or drug carriers first meet vasculature before extravasation in the tumor (Oku et al., 2002). The concept is that angiogenesis is a required step for the expansion during tumorogenesis. Similarly, angiogenesis accompanies diseases such as age-dependent macular degeneration. (Ng. et al., 2006). Because tumor vasculature expresses unique markers that distinguish it from normal vasculature (Hoffman et al., 2003), targeting based on these markers is a promising strategy for cancer treatment. These anti-angiogenic therapies have the promise of high efficacy and low toxicity. Moreover, delivery of chemotherapeutic drugs to tumor tissue based on affinity of a targeting ligand overcomes obstacles in cancer therapy caused by high tumor interstitial fluid pressure and drug resistance. Therefore, the disclosed peptides, which can be employed in ligand-targeted therapy, provide the bases for novel treatments that improve therapeutic effects over conventional anticancer drugs.

In vivo phage display was used to identify peptides that home specifically to tumor blood vessels. Table 1. The terms "home," "homing," "target," and "targeting" are used interchangeably in this application. Further study of one peptide, SP5-52, SVSVGMKPSPRP [SEQ ID NO: 2], revealed that this peptide recognized the vasculature in tumors but not in normal blood vessels in SCID mice bearing human tumors. It was discovered that SP5-52 could specifically bind not only with the tumor vessels of xenografts from multiple tumors in animal models but also with VEGF-stimulated human vascular endothelial cells (HUVECs) and with the blood vessels from human lung cancers. In addition, a SP5-52 peptide-linked liposome that carried doxorubicin (SP5-52-Lipo-Dox) enhanced the efficacy of the drug against human cancer xenografts in SCID mice. These studies indicate that the SP5-52-peptide can specifically bind to vasculature in multiple tumors, and is a good candidate for targeted drug delivery to solid tumors. SP5-52 and the other peptides are useful for targeting tumor vasculature.

Figure 1:
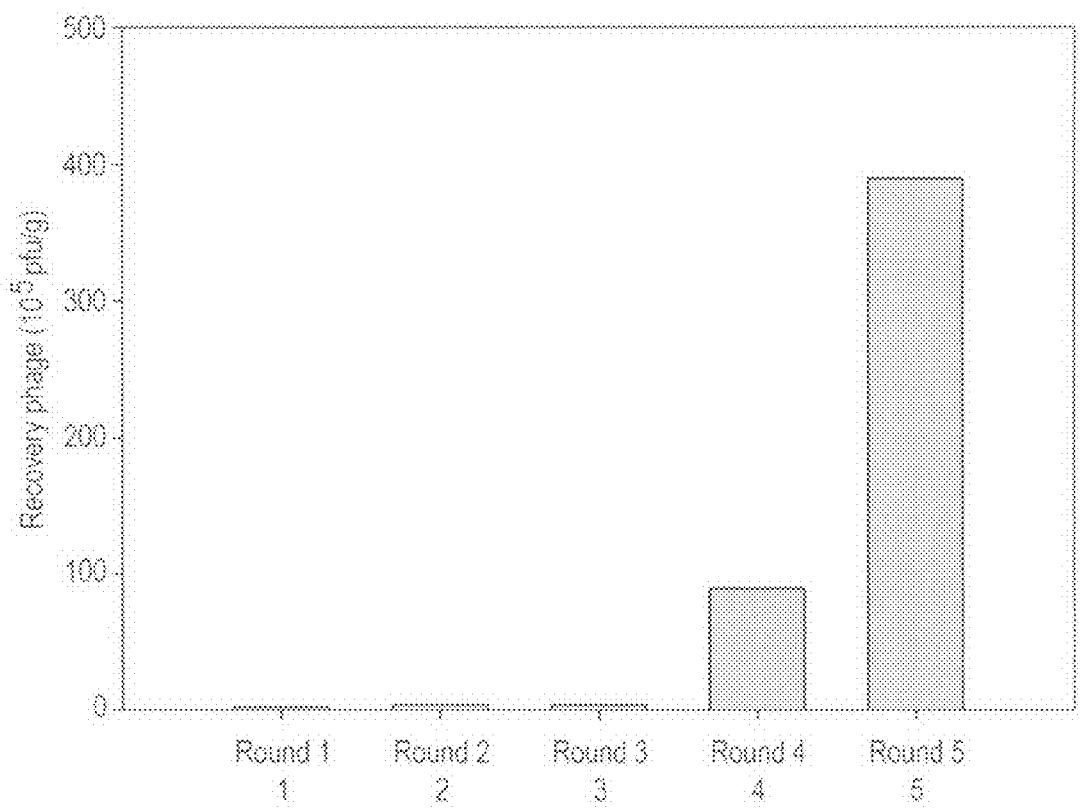
FIG. 1. Selection of lung cancer-targeting phage by in vivo phage display.

In our study, phages-from the fifth round of in vivo biopanning showed 156-fold higher binding activity with lung cancer xenografts than that of the initial phage library (FIG. 1). Specific phage clones displayed the consensus peptide motif, Proline-Serine-Proline (PSP) (Table 1). In a separate in vivo phage display experiment, we identified a phage clone, named IVO-2, which homed to tumor tissue of oral cancer xenografts. We determined that IVO-2 also displayed the same amino acid sequence as PC5-52.

Figure 2:
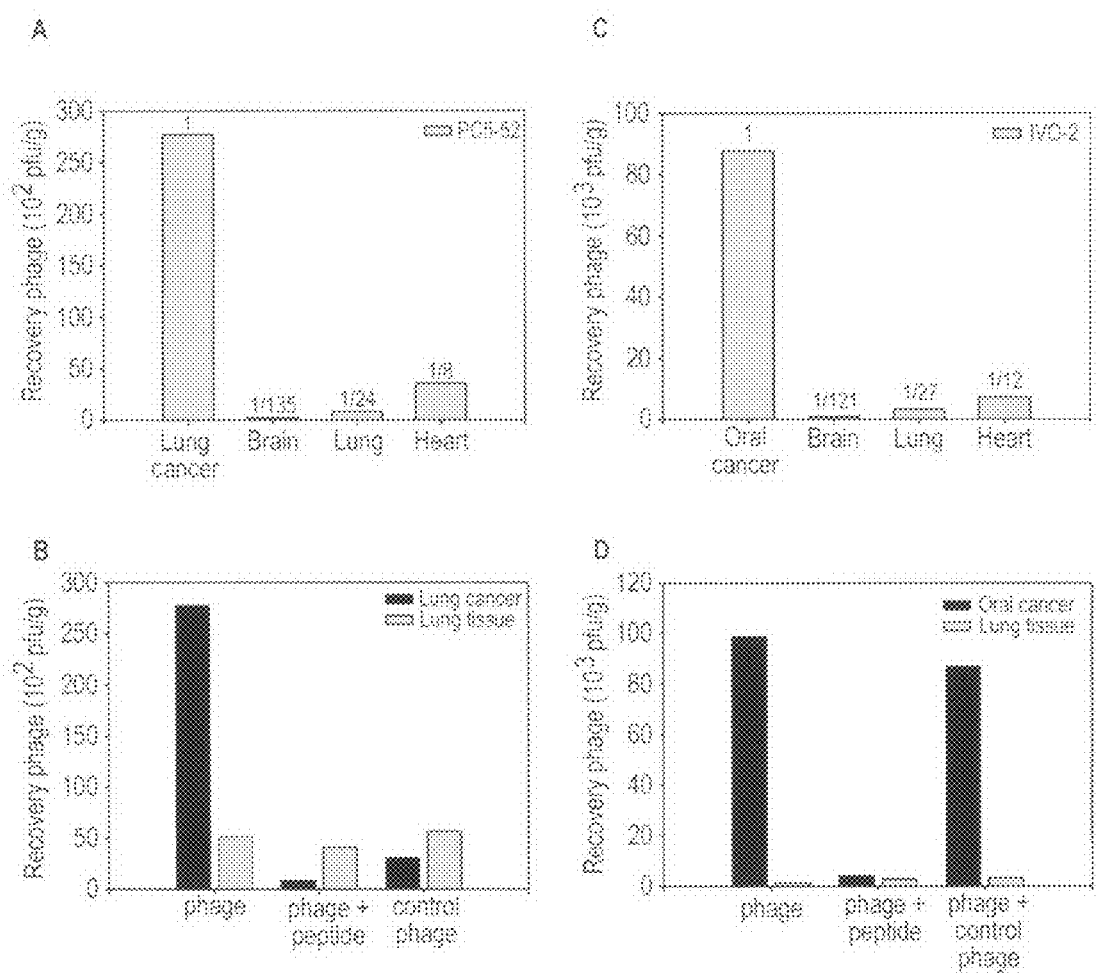
FIGS. 2 A-D. Specificity of tumor-homing phage. (A) Recovery of PC5-52 in selected organs. (B) Recovery of PC5-52 in selected organs in the presence of SP5-52. (C) Recovery of IVO-2 in selected organs. (D) Recovery of IVO-2 in selected organs in the presence of SP5-52.
Figure 3:
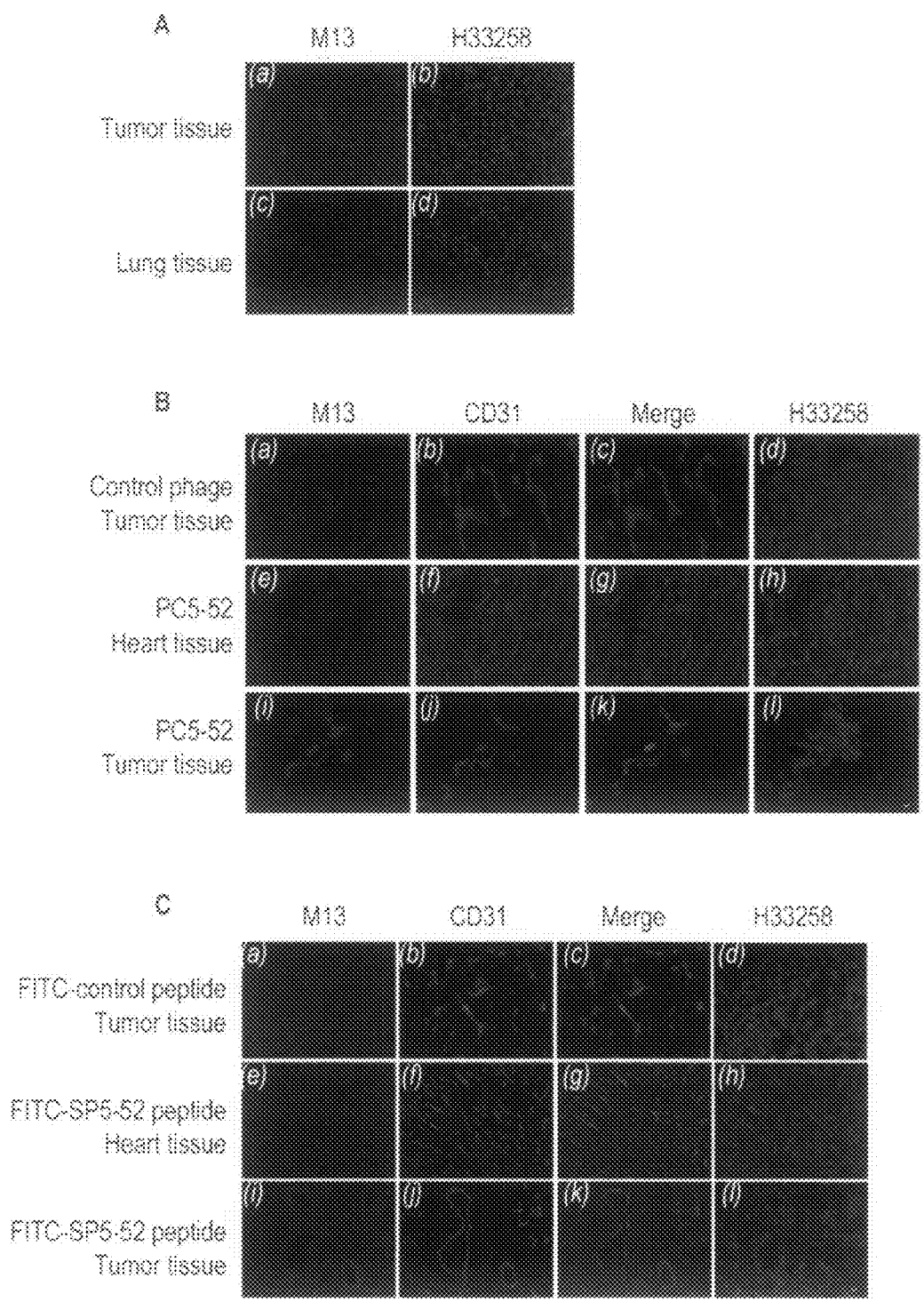
FIGS. 3 A-C. (A)(a)-(d) Immunofluorescent localization of PC5-52 phage after i.v. injection into human lung. (B)(a)-(j) Investigation of phage binding to tumor vessels of lung cancer xenografts. (C)(a)-(j) Binding of FITC-labeled SP5-52 peptide with tumor vessels of lung cancer xenografts.

An in vivo homing experiment showed that PC5-52 could specifically bind to vessels of tumor tissues from lung and oral cancer xenografts but not to other normal organs, such as lung, heart and brain (FIGS. 2 and 3). When a peptide competitive inhibition assay was performed, the binding activity of PC5-52 with tumor tissues was inhibited by synthetic peptide SP5-52 (FIGS. 2B and D). These results suggest that the synthetic peptides bind to the same binding sites as the respective phage clones.

To investigate the localization of homing phages in tumor masses and normal organs, PC5-52 was i.v. injected into SCID mice bearing lung cancer and frozen sections from these mice were then subjected to double localization using anti-mouse CD31 and anti-M13 mAbs. The results revealed that CD31 and phage particles colocalized in most xenograft vascular endothelia and rarely in tumor cells and other normal organs (FIG. 3). These results indicate that PC5-52 can specifically target endothelial cells of tumor vasculature but not to tumor cells or blood vessels of normal organs.

Figure 4:
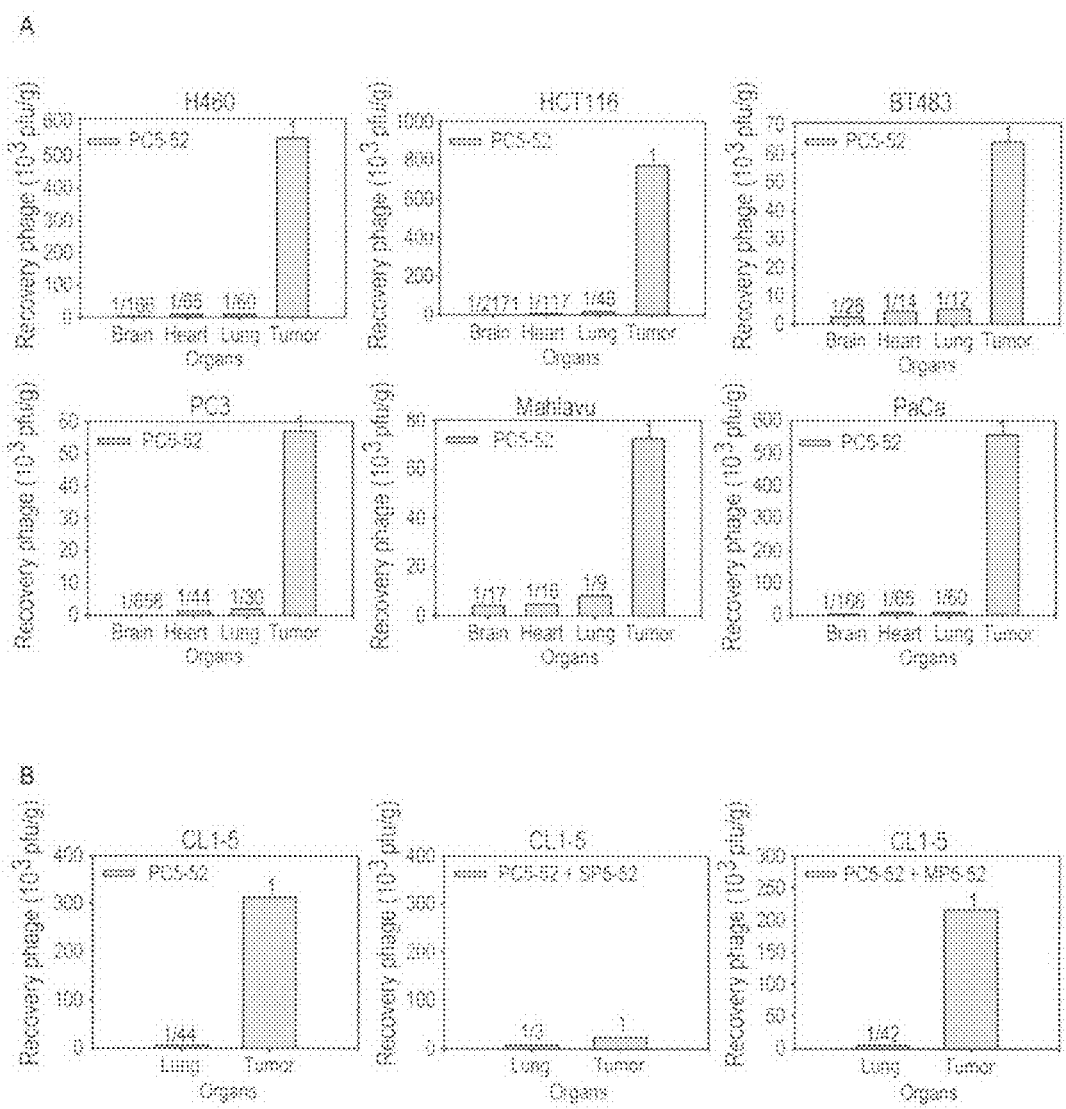
FIGS. 4 A and B. (A) Recovery of tumor-targeting phage PC5-52 from SCID mice bearing different human cancer xenografts. (B) Recovery of tumor-targeting phage PC5-52 from SCID mice bearing different human cancer xenografts in the absence and presence of SP5-52 and MP5-52.

We expanded our investigation to examine whether PC5-52 could also bind to the vasculature of xenografts derived from other human tumor cells, such as human lung (H460), colon (HCT116), breast (BT483), prostate (PC3), liver (Mahlavu) and pancreatic (PaCa) cancer cells. The results showed that these xenograft tumor tissues from different cancer cell lines contained a higher titer (over 10-fold compared with normal organs) of PC5-52 than normal organs (FIG. 4). These data indicate that PC5-52 has a higher affinity in binding to the tumor tissues from eight different types of human cancer xenografts. This phenomenon suggests that vasculature in solid tumors may express an unknown universal receptor that can be recognized by the SP5-52 peptide. Our demonstration that both PC5-52 phage and FITC-labeled SP5-52 peptide could bind specifically to tumor vascular endothelia in xenografts but not to normal blood vessels (FIG. 3) further supports this possibility.

To investigate the role of the consensus motif Proline (P)-Serine (S)-Proline (P), which is present in the displayed peptides of three clones shown in Table 1, PC5-5, PC-52 and PC-54, we changed these three amino acid residues in SP5-52 (SVSVGMKPSPRP) to GGG in mutant peptide MP5-52 (SVSVGMKGGGRP) [SEQ ID NO: 20]. As shown in FIG. 4B, the tumor homing ability of PC5-52 was markedly inhibited by SP5-52, but not by mutant peptide MP5-52 (FIG. 4B).

Figure 5:
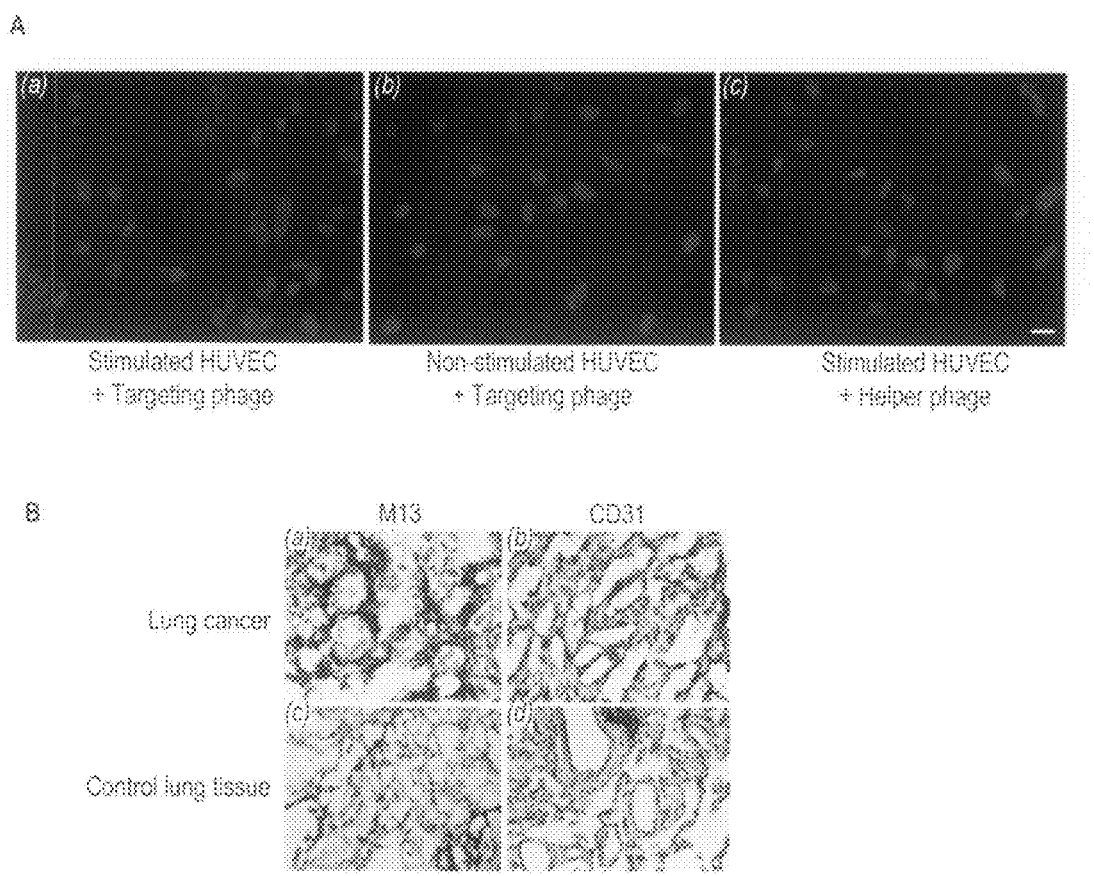
FIGS. 5 A and B. (A)(a)-(c) Targeting phages react with VEGF-stimulated HUVECs. (B)(a)-(c) Immunohistochemical localization of biotin-labeled SP5-52 peptide on lung adenocarcinoma specimens.

To evaluate the applicability of SP5-52 for human cancer therapy, we investigated whether the peptide selected in the murine angiogenic model has binding affinity for vasculature endothelia in human tumors. We confirmed that the peptide could specifically bind to VEGF-stimulated endothelial cells and to human lung cancer biopsy specimens (FIG. 5). Our results indicate that SP5-52 can be used as a targeting ligand for development of ligand-targeted therapy for human lung cancer or other cancers.

Figure 6:
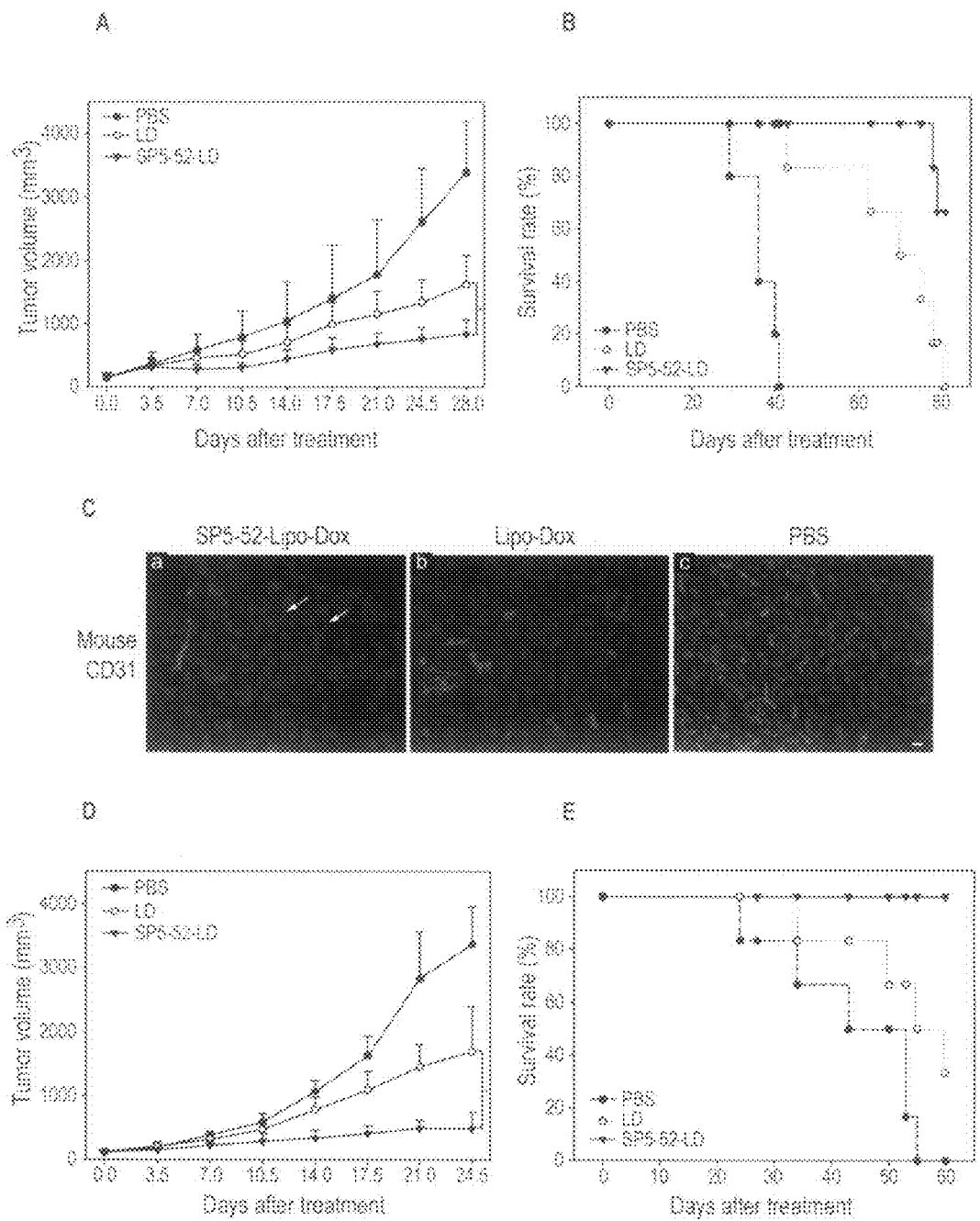
FIGS. 6 A-E. (A) Treatment of SCID mice bearing human lung cancer xenografts with SP5-52-Lipo-Dox. (B) Survival curve of SCID mice bearing human lung cancer xenografts treated with SP5-52-Lipo-Dox. (C) Decrease and damage of tumor vessels in the mice treated with SP5-52-Lipo-Dox. (D) Treatment of SCID mice bearing oral cancer xenografts with SP5-52-Lipo-Dox. (E) Survival curve of SCID mice bearing oral cancer xenografts with SP5-52-Lipo-Dox.

We prepared SP5-52-conjugated liposomes to compare the effect of a liposome comprising SP5-52 and doxorubicin, SP5-52-Lipo-Dox, and a liposome comprising doxorubicin, Lipo-Dox, on tumor growth. The results revealed that SP5-52-Lipo-Dox enhanced the efficacy of the drug against both human lung and oral cancer xenografts (FIGS. 6A and D). Furthermore, this targeting liposome also significantly increased the survival rate of these two human cancer animal models (FIGS. 6B and E). The tumor vasculature was destroyed and markedly decreased by SP5-52-Lipo-Dox treatment (FIG. 6C).

Figure 7:
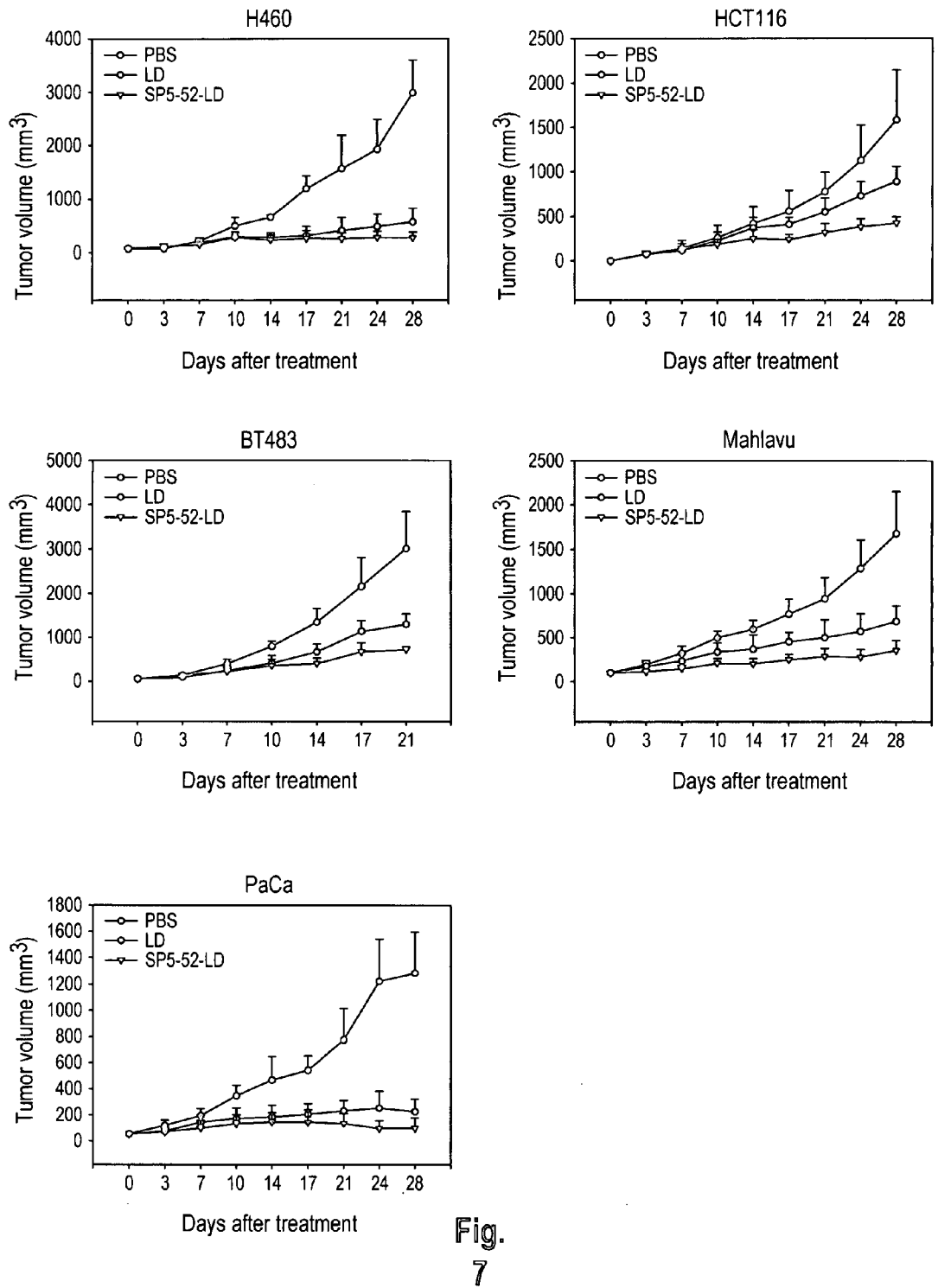
FIG. 7. Treatment of SCID mice bearing xenografts of various human cancers with SP5-52-Lipo-Dox.

To investigate whether SP5-52-Lipo-Dox could also enhance therapeutic efficacy to other solid tumors, we treated mice bearing xenografts from five types of human cancer, including human lung (H460), colon (HCT116), breast (BT483), liver (Mahlavu) and pancreatic (PaCa) cancer. Interestingly, the targeting liposome SP5-52-Lipo-Dox showed increased therapeutic efficacy for these five human cancers (FIG. 7). These results indicate that conjugation of Lipo-Dox with the peptide SP5-52 enhances the ability of the drugs to inhibit human solid tumor xenografts.

Thus, these new targeting strategies, including the ones described here, have the potential to markedly improve cancer treatment.

The tumor vasculature is a particularly suitable target for cancer therapy because it is composed of nonmalignant endothelial cells that are genetically stable and induce little or no drug resistance (Boehm et al., 1997). In addition, these cells are more accessible to drugs and have an intrinsic amplification mechanism. It has been estimated that elimination of a single endothelial cell can inhibit the growth of 100 tumor cells (Burrows and Thorpe., 1994; Denekamp, 1993). Our results proved that the tumor vasculature was destroyed and markedly decreased by SP5-52-Lipo-Dox treatment (FIG. 6C). These data clearly demonstrate that this targeting liposome improves the chemotherapeutic efficacy in a xenograft animal model. This effect may be due to the accumulation of targeting liposomes in tumor tissues. High tumor interstitial fluid pressure (IFP) of solid tumors is a barrier for efficient drug delivery (Heldin et al., 2004). Increased IFP contributes to decreased transcapillary transport in tumors, which leads to decreased uptake of drugs and results in the eventual failure of therapy. These phenomena are accompanied by the development of drug resistance and metastatic disease (Boucher et al., 1990; Boucher et al., 1991; Gutmann et al., 1992; Heldin et al., 2004; Less et al., 1992). The effective ligand-targeted therapy as described here, which utilizes the affinity of a ligand to carry anti-cancer drugs to tumor tissue, may function by increasing the accumulation of drugs despite high WFP of the tumor.

Using in vivo phage display to isolate the targeting ligands on molecules of tumor endothelial cells, we have identified several peptides, including PC5-52, which target to vasculature in two NSCLC and six human tumor xenografts. The liposome targeted via this peptide increased therapeutic efficacy of the liposome and increased the survival rate of mice bearing human lung and oral cancer xenografts. SP5-52 is an excellent agent for drug delivery to vasculature of solid tumors and can be applied to clinical cancer treatment.

REFERENCES

AFSA., H. (1966). Determination of free amino groups in protein by trinitrobenzene sulfuric acid. Anal Biochem 14, 328.

Arap, W., Pasqualini, R., and Ruoslahti, E. (1998). Cancer treatment by targeted drug delivery to tumor vasculature in a mouse model. Science 279, 377-380.

Atwell, S., Ultsch, M., De Vos, A. M., and Wells, J. A. (1997). Structural plasticity in a remodeled protein-protein interface. Science 278, 1125-1128.

Barry, M. A., Dower, W. J., and Johnston, S. A. (1996). Toward cell-targeting gene therapy vectors: selection of cell-binding peptides from random peptide-presenting phage libraries. Nat Med 2, 299-305.

Bergers, G., Song, S., Meyer-Morse, N., Bergsland, E., and Hanahan, D. (2003). Benefits of targeting both pericytes and endothelial cells in the tumor vasculature with kinase inhibitors. The Journal of clinical investigation 111, 1287-1295.

Boehm, T., Folkman, J., Browder, T., and O'Reilly, M. S. (1997). Antiangiogenic therapy of experimental cancer does not induce acquired drug resistance. Nature 390, 404-407.

Bottger, V., Bottger, A., Howard, S. F., Picksley, S. M., Chene, P., Garcia-Echeverria, C., Hochkeppel, H. K., and Lane, D. P. (1996). Identification of novel mdm2 binding peptides by phage display. Oncogene 13, 2141-2147.

Boucher, Y., Baxter, L. T., and Jain, R. K. (1990). Interstitial pressure gradients in tissue-isolated and subcutaneous tumors: implications for therapy. Cancer research 50, 4478-4484.

Boucher, Y., Kirkwood, J. M., Opacic, D., Desantis, M., and Jain, R. K. (1991). Interstitial hypertension in superficial metastatic melanomas in humans. Cancer research 51, 6691-6694.

Burrows, F. J., and Thorpe., P. E. (1994). Vascular targeting: A new approach to the therapy of solid tumors. Pharmacol Ther 64, 155-174.

Castano, A. R., Tangri, S., Miller, J. E., Holcombe, H. R., Jackson, M. R., Huse, W. D., Kronenberg, M., and Peterson, P. A. (1995). Peptide binding and presentation by mouse CD1. Science 269, 223-226.

Chu, Y. W., Yang, P. C., Yang, S. C., Shyu, Y. C., Hendrix, M. J., Wu, R., and Wu, C. W. (1997). Selection of invasive and metastatic subpopulations from a human lung adenocarcinoma cell line. American journal of respiratory cell and molecular biology 17, 353-360.

D'Mello, F., Partidos, C. D., Steward, M. W., and Howard, C. R. (1997). Definition of the primary structure of hepatitis B virus (HBV) pre-S hepatocyte binding domain using random peptide libraries. Virology 237, 319-326.

DeLeo, F. R., Yu, L., Burritt, J. B., Loetterle, L. R., Bond, C. W., Jesaitis, A. J., and Quinn, M. T. (1995). Mapping sites of interaction of p47-phox and flavocytochrome b with random-sequence peptide phage display libraries. Proc Natl Acad Sci USA 92, 7110-7114.

Denekamp, J. (1993). Angiogenesis, neovascular proliferation and vascular pathophysiology as targets for cancer therapy. Br J Radiol 66, 181-196.

Drummond, D. C., Meyer, O., Hong, K., Kirpotin, D. B., and Papahadjopoulos, D. (1999). Optimizing liposomes for delivery of chemotherapeutic agents to solid tumors. Pharmacological reviews 51, 691-743.

Dvorak, H. F., Nagy, J. A., and Dvorak, A. M. (1991). Structure of solid tumors and their vasculature: implications for therapy with monoclonal antibodies. Cancer Cells 3, 77-85.

Eliceiri, B. P., and Cheresh, D. A. (1999). The role of alphav integrins during angiogenesis: insights into potential mechanisms of action and clinical development. The Journal of clinical investigation 103, 1227-1230.

Essler, M., and Ruoslahti, E. (2002). Molecular specialization of breast vasculature: a breast-homing phage-displayed peptide binds to aminopeptidase P in breast vasculature. Proc Natl Acad Sci USA 99, 2252-2257.

Folgori, A., Tafi, R., Meola, A., Felici, F., Galfre, G., Cortese, R., Monaci, P., and Nicosia, A. (1994). A general strategy to identify mimotopes of pathological antigens using only random peptide libraries and human sera. Embo J 13, 2236-2243.

Fu, Y., Shearing, L. N., Haynes, S., Crewther, P., Tilley, L., Anders, R. F., and Foley, M. (1997). Isolation from phage display libraries of single chain variable fragment antibodies that recognize conformational epitopes in the malaria vaccine candidate, apical membrane antigen-1. J Biol Chem 272, 25678-25684.

Gabizon, A., and Martin, F. (1997). Polyethylene glycol-coated (pegylated) liposomal doxorubicin. Rationale for use in solid tumours. Drugs 54 Suppl 4, 15-21.

Gutmann, R., Leunig, M., Feyh, J., Goetz, A. E., Messmer, K., Kastenbauer, E., and Jain, R. K. (1992). Interstitial hypertension in head and neck tumors in patients: correlation with tumor size. Cancer research 52, 1993-1995.

Heldin, C. H., Rubin, K., Pietras, K., and Ostman, A. (2004). High interstitial fluid pressure-an obstacle in cancer therapy. Nature reviews 4, 806-813.

Hoffman, J. A., Giraudo, E., Singh, M., Zhang, L., Inoue, M., Porkka, K., Hanahan, D., and Ruoslahti, E. (2003). Progressive vascular changes in a transgenic mouse model of squamous cell carcinoma. Cancer cell 4, 383-391.

Kirpotin, D., Park, J. W., Hong, K., Zalipsky, S., Li, W. L., Carter, P., Benz, C. C., and Papahadjopoulos, D. (1997). Sterically stabilized anti-HER2 immunoliposomes: design and targeting to human breast cancer cells in vitro. Biochemistry 36, 66-75.

Koivunen, E., Arap, W., Rajotte, D., Lahdenranta, J., and Pasqualini, R. (1999). Identification of receptor ligands with phage display peptide libraries. J Nucl Med 40, 883-888.

Kraft, S., Diefenbach, B., Mehta, R., Jonczyk, A., Luckenbach, G. A., and Goodman, S. L. (1999). Definition of an unexpected ligand recognition motif for alphav beta6 integrin. J Biol Chem 274, 1979-1985.

Lee, T. Y., Wu, H. C., Tseng, Y. L., and Lin, C. T. (2004). A novel peptide specifically binding to nasopharyngeal carcinoma for targeted drug delivery. Cancer Res 64, 8002-8008.

Less, J. R., Posner, M. C., Boucher, Y., Borochovitz, D., Wolmark, N., and Jain, R. K. (1992). Interstitial hypertension in human breast and colorectal tumors. Cancer research 52, 6371-6374.

Li, B., Tom, J. Y., Oare, D., Yen, R., Fairbrother, W. J., Wells, J. A., and Cunningham, B. C. (1995). Minimization of a polypeptide hormone. Science 270, 1657-1660.

Liu, I. J., Hsueh, P. R., Lin, C. T., Chiu, C. Y., Kao, C. L., Liao, M. Y., and Wu, H. C. (2004). Disease-specific B Cell epitopes for serum antibodies from patients with severe acute respiratory syndrome (SARS) and serologic detection of SARS antibodies by epitope-based peptide antigens. J Infect Dis 190, 797-809.

Martin, F. J. (1998). Clinical pharmacology and antitumor efficacy of DOXIL (pegylated liposomal doxorubicin), in Medical Applications of Liposomes (Lasic DD and Papahadjopoulos D eds), (New York: Elsevier Science BV).

Mazzucchelli, L., Burritt, J. B., Jesaitis, A. J., Nusrat, A., Liang, T. W., Gewirtz, A. T., Schnell, F. J., and Parkos, C. A. (1999). Cell-specific peptide binding by human neutrophils. Blood 93, 1738-1748.

Nord, K., Gunneriusson, E., Ringdahl, J., Stahl, S., Uhlen, M., and Nygren, P. A. (1997). Binding proteins selected from combinatorial libraries of an alpha-helical bacterial receptor domain. Nat Biotechnol 15, 772-777.

Oku, N., Asai, T., Watanabe, K., Kuromi, K., Nagatsuka, M., Kurohane, K., Kikkawa, H., Ogino, K., Tanaka, M., Ishikawa, D., et al. (2002). Anti-neovascular therapy using novel peptides homing to angiogenic vessels. Oncogene 21, 2662-2669.

Papahadjopoulos, D., Allen, T. M., Gabizon, A., Mayhew, E., Matthay, K., Huang, S. K., Lee, K. D., Woodle, M. C., Lasic, D. D., Redemann, C., and et al. (1991). Sterically stabilized liposomes: improvements in pharmacokinetics and antitumor therapeutic efficacy. Proceedings of the National Academy of Sciences of the United States of America 88, 11460-11464.

Park, J. W., Hong, K., Kirpotin, D. B., Colbern, G., Shalaby, R., Baselga, J., Shao, Y., Nielsen, U. B., Marks, J. D., Moore, D., et al. (2002). Anti-HER2 immunoliposomes: enhanced efficacy attributable to targeted delivery. Clin Cancer Res 8, 1172-1181.

Pasqualini, R., Koivunen, E., and Ruoslahti, E. (1995). A peptide isolated from phage display libraries is a structural and functional mimic of an RGD-binding site on integrins. J Cell Biol 130, 1189-1196.

Pasqualini, R., Koivunen, E., and Ruoslahti, E. (1997). Alpha v integrins as receptors for tumor targeting by circulating ligands. Nature biotechnology 15, 542-546.

Pasqualini, R., and Ruoslahti, E. (1996). Organ targeting in vivo using phage display peptide libraries. Nature 380, 364-366.

Prezzi, C., Nuzzo, M., Meola, A., Delmastro, P., Galfre, G., Cortese, R., Nicosia, A., and Monaci, P. (1996). Selection of antigenic and immunogenic mimics of hepatitis C virus using sera from patients. J Immunol 156, 4504-4513.

Ruoslahti, E. (2002). Specialization of tumour vasculature. Nature reviews 2, 83-90.

Scott, J. K., and Smith, G. P. (1990). Searching for peptide ligands with an epitope library. Science 249, 386-390.

Shockley, T. R., Lin, K., Nagy, J. A., Tompkins, R. G., Dvorak, H. F., and Yarmush, M. L. (1991). Penetration of tumor tissue by antibodies and other immunoproteins. Annals of the New York Academy of Sciences 618, 367-382.

Smith, W. C., McDowell, J. H., Dugger, D. R., Miller, R., Arendt, A., Popp, M. P., and Hargrave, P. A. (1999). Identification of regions of arrestin that bind to rhodopsin. Biochemistry 38, 2752-2761.

Speth, P. A., van Hoesel, Q. G., and Haanen, C. (1988). Clinical pharmacokinetics of doxorubicin. Clinical pharmacokinetics 15, 15-31.

Tseng, Y. L., Hong, R. L., Tao, M. H., and Chang, F. H. (1999). Sterically stabilized anti-idiotype immunoliposomes improve the therapeutic efficacy of doxorubicin in a murine B-cell lymphoma model. International journal of cancer 80, 723-730.

Wrighton, N. C., Farrell, F. X., Chang, R., Kashyap, A. K., Barbone, F. P., Mulcahy, L. S., Johnson, D. L., Barrett, R. W., Jolliffe, L. K., and Dower, W. J. (1996). Small peptides as potent mimetics of the protein hormone erythropoietin. Science 273, 458-464.

Wu, H. C., Huang, Y. L., Chao, T. T., Jan, J. T., Huang, J. L., Chiang, H. Y., King, C. C., and Shaio, M. F. (2001). Identification of B-cell epitope of dengue virus type I and its application in diagnosis of patients. J Clin Microbiol 39, 977-982.

Wu, H. C., Jung, M. Y., Chiu, C. Y., Chao, T. T., Lai, S. C., Jan, J. T., and Shaio, M. F. (2003). Identification of a dengue virus type 2 (DEN-2) serotype-specific B-cell epitope and detection of DEN-2-immunized animal serum samples using an epitope-based peptide antigen. J Gen Virol 84, 2771-2779.

Zalipsky, S., Mullah, N., Harding, J. A., Gittelman, J., Guo, L., and DeFrees, S. A. (1997). Poly(ethylene glycol)-grafted liposomes with oligopeptide or oligosaccharide ligands appended to the termini of the polymer chains. Bioconjugate chemistry 8, 111-118.

DEFINITIONS

The terms used herein have their ordinary meanings, as set forth below, and can be further understood in the context of the specification.

The terms "polynucleotide," "nucleotide," "nucleic acid," "nucleic acid molecule," "nucleic acid sequence," "polynucleotide sequence," and "nucleotide sequence" are used interchangeably herein to refer to polymeric forms of nucleotides of any length. The polynucleotides can comprise deoxyribonucleotides, ribonucleotides, and/or their analogs or derivatives. The term includes variants. Variants may include insertions, additions, deletions, or substitutions. Nucleotide sequences shown herein are listed in the 5' to 3' direction.

The terms "polypeptide," "peptide," and "protein," used interchangeably herein, refer to a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. The term includes single chain protein as well as multimers. The term also includes proteins conjugated to a label such as FITC, biotin, and radioisotopes, including, but not limited to $^{64}$Cu, $^{67}$Cu, $^{90}$Y, $^{99}$mTc, $^{111}$In, $^{124}$I, $^{125}$I, $^{131}$I, $^{137}$cS, $^{186}$Re, $^{211}$At, $^{212}$Bi, $^{213}$Bi, $^{223}$Ra, $^{241}$Am, and $^{244}$Cm; enzymes having detectable products (for example, luciferase, peroxidase, alkaline phosphatase, β-galactosidase, and the like); fluorescers and fluorescent labels, fluorescence emitting metals, for example, $^{152}$Eu, or others of the lanthanide series, electrochemiluniescent compounds, chemiluminescent compounds, for example, luminol, isoluminol, or acridinium salts; specific binding molecules, for example, magnetic particles, microspheres, nanospheres, and the like. The term also includes peptides conjugated to therapeutic agents.

The term also includes fusion proteins, including, but not limited to, glutathione S-transferase (GST) fusion proteins, fusion proteins with a heterologous amino acid sequence such as bioluminescent proteins, for example, luciferin, or aequorin (green fluorescent protein), with heterologous and homologous leader sequences, fusion proteins with or without N-terminal methionine residues, pegylated proteins, and immunologically tagged, or his-tagged proteins. Such fusion proteins also include fusions to epitopes. Such fusion proteins can comprise multimers of the peptides of the invention, e.g. homodimers or homomultimers, and heterodimers and heteromultimers. The term also includes peptide aptamers.

Peptides of the invention include biologically active variants of the peptides, where such variants are substantially similar in structure. Variants of peptide sequences may include insertions, additions, deletions, or substitutions compared with the subject peptides. Variants of polypeptide sequences include biologically active polymorphic variants.

Peptides of the invention can include naturally-occurring and non-naturally occurring amino acids. Peptides can comprise D-amino acids, a combination of D- and L-amino acids, and various "designer" or "synthetic" amino acids (for example, β-methyl amino acids, Cα-methyl amino acids, and Nα-methyl amino acids, etc.) to convey special properties. Additionally, peptides can be cyclic. Peptides can include non-classical amino acids in order to introduce particular conformational motifs. Any known non-classical amino acid can be used. Amino acid analogs and peptidomimetics can be incorporated into a peptide to induce or favor specific secondary structures, including, but not limited to, LL-Acp (LL-3-amino-2-propenidone-6-carboxylic acid), α-turn inducing dipeptide analog; α-sheet inducing analogs; βturn inducing analogs; α-helix inducing analogs; γ-turn inducing analogs; Gly-Ala turn analogs; amide bond isostere; or tretrazol, and the like.

A desamino or descarboxy residue can be incorporated at the terminal ends of the peptide, so that there is no terminal amino or carboxyl group, to decrease susceptibility to proteases or to restrict conformation. C-terminal functional groups include amide, amide lower alkyl, amide di (lower alkyl), lower alkoxy, hydroxy, and carboxy, and the lower ester derivatives thereof, and the pharmaceutically acceptable salts thereof.

The term "liposome" refers to a composition comprising an outer lipid bi-layer or multi-layer membrane surrounding an internal aqueous space. The term includes multilamellar liposomes, which generally have a diameter in the range of about one to about ten micrometers and comprise anywhere from two to hundreds of concentric lipid bilayers alternating with layers of an aqueous phase. The term includes unilamellar vesicles which are comprised of a single lipid layer and generally have a diameter in the range of about 20 to about 400 nanometers (nm), about 50 to about 300 nm, about 300 to about 400 nm, or about 100 to about 200 nm. The term also includes liposomes with diameters from about 65 nm to about 75 nm.

The terms "antibody" and "immunoglobulin" refer to a protein, for example, one generated by the immune system, synthetically, or recombinantly, that is capable of recognizing and binding to a specific antigen. Antibodies are commonly known in the art, and can be prepared by methods known in the art.

An "epitope" is a molecule to which an antibody binds, which may or may not be a contiguous sequence of amino acid residues in a polypeptide, and which may comprise sugars and/or molecules having other chemical structures.

The term "hybridizes specifically," in the context of a polynucleotide, refers to hybridization under stringent conditions. Conditions that increase stringency of both DNA/DNA and DNA/RNA hybridization reactions are widely known and published in the art. Examples of stringent hybridization conditions include hybridization in 4× sodium chloride/sodium citrate (SSC), at about 65-70° C., or hybridization in 4×SSC plus 50% formamide at about 42-50° C., followed by one or more washes in 1×SSC, at about 65-70° C.

The term "ligand" refers to a molecule that binds to another molecule, including a receptor.

A "host cell" is an individual cell or cell culture which can be or has been a recipient of any recombinant vector(s) or isolated polynucleotide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention may be called a "recombinant host cell."

A "specimen" is any biological specimen derived from a patient; the term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization, or enrichment for certain components, such as polynucleotides or polypeptides. Also included in the term are derivatives and fractions of patient samples. A patient sample may be used in a diagnostic, prognostic, or other monitoring assay. The term also applies to a biological specimen from a non-human mammal. The specimen can be from a human patient or a non-human mammal.

"Treatment," as used herein, covers any administration or application of remedies for disease in a mammal, including a human, and includes inhibiting the disease, arresting its development, or relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse affect attributable to the disorder. Thus, the invention provides both treatment and prophylaxis. It includes (1) preventing the disorder from occurring or recurring in a subject who may be predisposed to the disorder but is not yet symptomatic, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or tumor size.

A "pharmaceutically acceptable carrier" refers to a nontoxic solid, semisolid or liquid filler, diluent, encapsulating material, formulation auxiliary, or excipient of any conventional type. A pharmaceutically acceptable carrier is nontoxic to recipients at the dosages and concentrations employed and is compatible with other ingredients of the formulation.

A "composition" herein refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses, or powders.

"Disease" refers to any condition, infection, disorder, or syndrome that requires medical intervention or for which medical intervention is desirable. Such medical intervention can include treatment, diagnosis, and/or prevention.

"Cancer" is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term cancer includes lung cancer, colon cancer, breast cancer, prostate cancer, liver cancer, pancreatic cancer, and oral cancer.

"Macular degeneration" includes growth of inappropriately regulated, leaky blood vessels and includes age-related macular degeneration (AMD), proliferative diabetic retinopathy (PDR), and retinopathy of prematurity (ROP).

Cell Lines

Useful cell lines include A549, human lung squamous cell carcinoma line, CL1-5, high metastatic human lung adenocarcinoma line, H23, human lung adenocarcinoma line, H460, human lung large cell carcinoma line, PC13, human lung cancer line, NPC-TWO1, human nasopharyngeal carcinoma line, SAS, human oral squamous cell carcinoma line, PaCa, human pancreas carcinoma, colon (HCT116), breast (BT483), prostate (PC3), liver (Mahlavu), NNM, human normal nasal mucosal epithelia, and fibroblast. A549, H23, H460, PC13, PaCa, HCT116, PC3, Mahlavu and SAS are available from the American Type Culture Collection. CL1-5 and NPC-TW01 cell lines were established by (Chu et al., 1997) and (Lin et al., 1990), respectively.

Preparation of Peptides

The peptides of the invention can be expressed using methods known in the art. Cell-based methods and cell-free methods are suitable for producing peptides of the invention. Cell-based methods generally involve introducing a nucleic acid construct into a host cell in vitro and culturing the host cell under conditions suitable for expression, then harvesting the peptide, either from the culture medium or from the host cell, (for example, by disrupting the host cell), or both. The invention also provides methods of producing a peptide using cell-free in vitro transcription/translation methods, which are well known in the art.

Suitable host cells include prokaryotic or eukaryotic cells, including, for example, bacterial, yeast, fungal, plant, insect, and mammalian cells.

Typically, a heterologous peptide, whether modified or unmodified, may be expressed on its own, as described above, or as a fusion protein, and may include not only secretion signals, but also a secretory leader sequence. A secretory leader sequence of the invention may direct certain proteins to the ER. The ER separates the membrane-bound proteins from other proteins. Once localized to the ER, proteins can be further directed to the Golgi apparatus for distribution to vesicles; including secretory vesicles; the plasma membrane, lysosomes, and other organelles.

Additionally, peptide moieties and/or purification tags may be added to the peptides. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, polyhistidines, avidin, and biotin. Conjugation of peptides to compounds such as biotin can be accomplished using techniques well known in the art. (Hermanson ed. (1996) Bioconjugate Techniques; Academic Press). Peptides can also be conjugated with radioisotopes, toxins, enzymes, fluorescent labels, colloidal gold, nucleic acids, vinorelbine, and doxorubicin using techniques known in the art. (Hermanson ed. (1996) Bioconjugate Techniques; Academic Press; Stefano et al. (2006) A conjugate of doxorubicin with lactosaminated albumin enhances the drug concentrations in all the forms of rat hepatocellular carcinomas independently of their differentiation grade. Liver Int. 26:726-33). Toxins those known in the art. Kreitman and Pastan, Immunotoxins in the treatment of hematologic malignancies. Curr Drug Targets. 7:1301-11 (2006).

Fusion partners suitable for use in the invention include, for example, fetuin, human serum albumin, Fc, and/or one or more of their fragments. Conjugated proteins, such as polyethylene glycol conjugates, are also provided.

The peptides of the invention can also be chemically synthesized using techniques known in the art (e.g., see Hunkapiller et al., Nature, 310:105 111 (1984); Grant ed. (1992) Synthetic Peptides, A Users Guide, W.H. Freeman and Co.; U.S. Pat. No. 6,974,884)). For example, a polypeptide corresponding to a fragment of a polypeptide can be synthesized by use of a peptide synthesizer or through the use of solid-phase methods known in the art.

Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

A peptide or peptidomimetic of the invention can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran, and dextran derivatives. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zalipsky, S. (1995) Bioconjugate Chem., 6:150-165; Monfardini, C., et al. (1995) Bioconjugate Chem. 6:62-69; U.S. Pat. Nos. 4,640,835; 4,496,689; 4,301,144; 4,670,417; 4,791,192; 4,179,337, or WO 95/34326.

Preparation of Liposomes

A variety of methods for preparing liposomes are known in the art, several of which are described by Lichtenberg and Barenholz in Methods of Biochemical Analysis, Volume 33, 337-462 (1988). Small unilamellar vesicles (SUV, size <100 nm) can be prepared by a combination of standard methods of thin-film hydration and repeated extrusion as described before (Tseng et al., 1999). Preparation methods particularly involving the encapsulation of DNA by liposomes, and methods that have a direct application to liposome-mediated transfection, have been described by Hug and Sleight et al (1991). Methods of making liposomes are also disclosed in U.S. Pat. No. 6,355,267 and U.S. Pat. No. 6,663,885. Liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

Liposomes are also commercially available from sources such as the Taiwan Liposome Company, Taipei Taiwan. Additional commercially available liposomes include TLC-D99, Lipo-Dox, Doxil, DaunoXome, AmBisome, ABELCET, transfectace (DDAB/DOPE) and DOTAP/DOPE and Lipofectin.

The liposomes of the present invention are most frequently prepared from phospholipids, but other molecules of similar molecular shape and dimensions having both a hydrophobic and a hydrophilic moiety can be used. For the purposes of the present invention, all such suitable liposome-forming molecules will be referred to herein as lipids. One or more naturally occurring and/or synthetic lipid compounds may be used in the preparation of the liposomes.

Liposomes may be anionic, cationic or neutral depending upon the choice of the hydrophilic group. For instance, when a compound with a phosphate or a sulfate group is used, the resulting liposomes will be anionic. When amino-containing lipids are used, the liposomes will have a positive charge, and will be cationic liposomes.

Representative suitable phospholipids or lipid compounds for forming initial liposomes useful in the present invention include, but are not limited to, phospholipid-related materials such as phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol. Additional nonphosphorous-containing lipids include, but are not limited to, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, diacylglycerolsuccinate, and the like.

Liposomal preparations for use in the instant invention include cationic (positively charged), anionic (negatively charged), and neutral preparations.

Remote loading of compounds into liposomes employs formation of transmembrane gradients (Ceh and Lasic, 1995). This method includes incubating the compound to be loaded into the liposomes and a boronic acid compound with suspended liposomes, thereby achieving accumulation of the compound within the liposomes (Zalipsky et al., 1998; Ceh B. and Lasic D. D., 1995; Zalipsky et al 1998; U.S. Pat. No. 6,051,251).

A phosphate assay can be used to determine liposome concentration. One phosphate assay is based on the interaction between molybdate and malachite green dye. The main principle involves the reaction of inorganic phosphate with molybdate to form a colorless unreduced phosphomolybdate complex which is converted to a blue colored complex when reduced under acidic conditions. Phosphomolybdate gives 20 or 30 times more color when complexed with malachite green. The final product, reduced green soluble complex is measured by its absorbance at 620 nm and is a direct measure of inorganic phosphate in solution.

In some embodiments, the liposomes are provided in formulation with pharmaceutically acceptable carriers, excipients, and diluents, of which a wide variety are known in the art. These pharmaceutical carriers, excipients, and diluents include those listed in the USP pharmaceutical excipients listing. USP and NF Excipients, Listed by Categories, p. 2404-2406, USP 24 NF 19, United States Pharmacopeial Convention Inc., Rockville, Md. (ISBN 1-889788-03-1). Pharmaceutically acceptable excipients, such as vehicles, adjuvants, carriers, or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents can be added as necessary. Percutaneous penetration enhancers such as Azone can also be included.

In pharmaceutical dosage forms, the compositions of the invention can be administered in the form of their pharmaceutically acceptable salts, or they can also be used alone or in appropriate association, as well as in combination, with other pharmaceutically active compounds. The subject compositions are formulated in accordance to the mode of potential administration.

Methods of Treatment

Peptides or liposomes of the invention comprising therapeutic drugs may be administered to a subject in need of treatment by injection systemically, such as by intravenous injection; or by injection or application to the relevant site, such as by direct injection into a tumor, or direct application to the site when the site is exposed in surgery; or by topical application, such as if the disorder is on the skin, for example. A subject in need of treatment includes a subject suffering from a disease accompanied by neovascularization, such as cancer, age-related macular degeneration, proliferative diabetic retinopathy, and retinopathy of prematurity.

Peptides or liposomes of the invention can be used as monotherapy. Alternatively, the peptides or liposomes of the invention can be used in combination with standard chemotherapeutic or radiation regimens to treat cancers, or therapies for diseases such as age-related macular degeneration.

The peptides of the invention could be used to target antibodies to vasculature for treatment. In one embodiment, a peptide of the invention is administered to a subject in need of treatment, followed by administration of an antibody that binds specifically to the peptide. The targeted antibodies may mediate antibody-dependent cell cytotoxicity or complement-dependent cytotoxicity, or may modify the underlying function of the target molecule. Such antibodies can be used in the form of antibody conjugates to directly deliver agents with a therapeutic effect on the target tissue. Such agents include radionuclides, toxins, chemotherapeutics, anti-VEGF aptamers and anti-angiogenic compounds.

Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid, or gaseous forms, such as tablets, capsules, powders, granules, ointments, solutions, suppositories, injections, inhalants and aerosols. The following methods and excipients are merely exemplary and are in no way limiting.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. The composition or formulation to be administered will, in any event, contain a quantity of the agent adequate to achieve the desired state in the subject being treated.

The liposomes or peptides of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. Other formulations for oral or parenteral delivery can also be used, as conventional in the art.

The liposomes or peptides of the invention may comprise one or more of the wide variety of drugs that have been employed in cancer treatment and inhibition of angiogenesis, including, but are not limited to, vinorelbine, cisplatin, gemcitabine, paclitaxel, etoposide, Novantrone (mitoxantrone), actinomycin D, camptothecin (or water soluble derivatives thereof), methotrexate, mitomycins (for example, mitomycin C), dacarbazine (DTIC), cyclophosphamide, and anti-neoplastic antibiotics such as doxorubicin and daunomycin, or others, described, for example, in (De Vita et al., 2001). The liposomes or peptides can also comprise cytotoxic drugs, oligonucleotides, toxins and radioactive molecules. The liposomes or peptides may also comprise compounds such as anti-VEGF aptamers described in (Ng et al 2006).

Drugs employed in cancer therapy may have a cytotoxic or cytostatic effect on cancer cells, or may reduce proliferation of the malignant cells. Drugs employed in cancer treatment can also be peptides. A liposome or peptide of the invention can be combined with radiation therapy. A liposome or peptide of the invention may be used adjunctively with therapeutic approaches described in De Vita, et al., eds. (2001). For those combinations in which a liposome or peptide of the invention and a second anti-cancer agent exert a synergistic effect against cancer cells, the dosage of the second agent may be reduced, compared to the standard dosage of the second agent when administered alone. A method for increasing the sensitivity of cancer cells comprises co-administering a liposome or peptide of the invention with an amount of a chemotherapeutic anti-cancer drug that is effective in enhancing sensitivity of cancer cells. Co-administration may be simultaneous or non-simultaneous administration. A liposome or peptide of the invention may be administered along with other therapeutic agents, during the course of a treatment regimen. In one embodiment, administration of a liposome or peptide of the invention and other therapeutic agents is sequential. An appropriate time course may be chosen by the physician, according to such factors as the nature of a patient's illness, and the patient's condition.

Diagnostic Methods

Detection of disease-specific biomarkers provides an effective screening strategy. Early detection provides not only early diagnosis, but in the case of cancer, can provide the ability to screen for polymorphisms and detect post-operative residual tumor cells and occult metastases, an early indicator of tumor recurrence. Early detection of disease-specific biomarkers can thus improve survival in patients before diagnosis, while undergoing treatment, and while in remission.

The peptides of the invention can be used as a diagnostic or prognostic for diseases, including cancer and other diseases accompanied by neovascularization. The peptides can be used as diagnostics in a number of ways, including but not limited to ELISA, Western blot, fluorescence, immunofluorescence, immunohistochemistry, or autoradiography.

The antibodies of the present invention can also be used in combination with the peptides of the invention to detect vasculature. In some embodiments, the assay is a binding assay that detects binding of an antibody with a peptide of the invention that has bound a vascular marker. The subject polypeptide or antibody can be immobilized, while the subject polypeptide and/or antibody can be detectably labeled. For example, the antibody can be directly labeled or detected with a labeled secondary antibody. That is, suitable, detectable labels for antibodies include direct labels, which label the antibody to the protein of interest, and indirect labels, which label an antibody that recognizes the antibody to the protein of interest. In another embodiment, the peptide comprises a label, and the binding of the peptide to a tissue is detected by assaying for the presence of the label.

Screening Methods

The invention provides a methods for identifying biological ligands that bind to peptides of the invention.

In one method, the peptides of the invention can be used as "bait proteins" in a two-hybrid assay or three-hybrid assay (see, e.g., U.S. Pat. No. 5,283,317; Zervos et al. (1993); Madura et al. (1993); Bartel et al. (1993); Iwabuchi et al. (1993); and Suter et al. (2006) to identify other proteins, which bind to or interact with peptides of the invention.

In another method, peptides of the invention are incubated with cellular extracts and molecules that bind to peptides of the invention are identified. In one method, the peptides of the invention are immobilized on a solid support, such as an HPLC column, and cellular extracts are exposed to immobilized peptides under conditions facilitating the binding of the peptides of the invention to target molecules. Bound molecules are eluted and identified through standard techniques such as mass-spectrometry. In one embodiment, the cellular extract comprises VEGF-stimulated HUVECs.

Affinity Purification of Target Protein

Proteins are extracted from lung cancer cells at 4° C. for 30 min with lysis buffer (50 mM Tris-HCl, pH 7.4, 150 mM NaCl, 30 µg/ml DNase, 1% Nonidet P-40, and protease inhibitors (Complete tabs; Roche Molecular Biochemicals). Protein lysates are cleared of debris by centrifugation at 15,000×g for 20 min. The lysates are first precleared on a 1-ml column containing control peptide, and the flow-through is directly applied onto a second 1-ml column of SP5-52 or SP5-2 peptide-immobilized affinity column. Columns are washed and eluted. The purity of the isolated protein is monitored by SDS-PAGE (8% polyacrylamide) and visualized by silver staining. The desired protein bands are cut out from the gel for in-gel digestion with trypsin. The resultant polypeptides are further analyzed by mass spectrometry.

EXAMPLES

The Examples, which are intended to be purely exemplary of the invention and should therefore not be considered to limit the invention in any way, also describe and detail aspects and embodiments of the invention discussed above.

Example 1

In Vivo Phage Display Biopanning Procedures

CL1-5, H460, and PC3 were grown in RPMI 1640 supplemented with 2 g bicarbonate, 40 mg kanamycin per liter, 2 mM L-glutamine, and 10% fetal bovine serum (FCS, Gibco, Calif., USA) at 37° C. under a humidified atmosphere of 95% air and 5% $CO_2$ (v/v). CL1-5 was established by Chu et al. (Chu et al., 1997). SAS, HCT116, BT483, Mahlavu and PaCa were grown in DMEM (Gibco, Calif., USA) containing 3.7 g bicarbonate, 40 mg kanamycin per liter, 2 mM L-glutamine, 5% FCS, and incubated in 10% $CO_2$ incubator. HUVECs were isolated from the umbilical vein after separation from the placenta and grown in M199 medium (Gibco, Calif., USA) supplemented with 20% FCS, antibiotics, 15 µg/ml endothelial growth factors (upstate, NY, USA), and incubated in a 5% $CO_2$ incubator.

To isolate tumor-homing phages from tumor tissues we used a phage displayed peptide library to treat the NSCLC (CL1-5) tumor-bearing mice for five rounds of in vivo selection (biopanning). SCID mice 4-6 weeks of age were injected subcutaneously into the dorsolateral flank with CL1-5 cells separately to produce lung cancer xenografts. A phage-displayed peptide library (New England Biolabs, Inc. MA, USA) was injected into the tail vein of SCID mice bearing size-matched CL1-5-derived tumors (~500 $mm^3$). After eight minutes of phage circulation, the mice were treated with diethyl ether to drive them into deep anesthesia, and perfused with 50 ml PBS to wash unbound phage. The organs (such as lung, heart, brain) and tumor masses were removed, weighed and washed with cold PBS. The organs and tumor samples were homogenized and the phage particles were rescued by ER2738 bacteria (New England BioLabs, Mass., USA). The phages were titered on agar plates in the presence of 1 mg/L of IPTG/X-Gal. The bound phages were amplified and titered in ER2738 culture. Recovered phages were subjected to four consecutive rounds of biopanning using SCID mice bearing lung cancer xenografts as above. The phages eluted from the fifth round were titered on LB/IPTG/X-Gal plates. The candidate tumor homing phage clones were randomly selected and identified by cellular ELISA and in vivo homing experiments.

The selected phage clones were further analyzed by DNA sequencing. The DNA sequences of purified phages were determined according to the dideoxynucleotide chain termination method using an automated DNA sequencer (ABI PRISM 377, Perkin-Elmer, Calif., USA). The sequencing was performed with prime5'-CCCTCATAGTTAGCG-TAACG-3' [SEQ ID NO: 19] corresponding to the pIII gene sequence. The phage-displayed peptide sequences were translated and aligned using Genetics Computer Group (GCG) program.

The recovery rate of the fifth round of biopanning increased to 156-fold over that of the first round (FIG. 1). These enriched phages were randomly selected and sequenced. Using GCG software, these nine had consistent residue Proline (P), while 4 clones (PC5-10, PC-53, PC-58 and PC-60) were found to have consensus amino acid residues, Serine (S)-Proline (P); 3 clones (PC5-5, PC-52 and PC-54) were found to have a consensus motif of Proline (P)-Serine (S)-Proline (P) (Table 1). Among the consensus peptide motifs tested in our phage-homing system, the phage clone PC5-52 was selected from both lung and oral (named IVO-2) tumor-bearing mice by in vivo phage display (Table 1 and FIG. 2C). The isolation of the same phage clone from two different human cancer (lung and oral) xenografts indicates that the peptide displayed on PC5-52 can target multiple solid tumors.

Example 2

In Vivo Homing and Peptide Binding in Xenograft Tumor Vessels

To investigate the targeting ability of PC5-52, phages were injected into the tail vein of SCID mice bearing human lung cancer cell-derived tumors and recovered after perfusion. We determined the titers of the phages in tumor mass and other normal organs. The phage clones, or control helper phage (insertless phage), were injected into the tail vein (i.v.) of SCID mice bearing human lung cancer tumor xenografts for 8 min or 24 h. After perfusion, xenograft tumors and organs were removed and the recovered phage titered. In peptide competitive inhibition experiments, described below, phage clones were co-injected with 100 μg synthetic peptide. After injection of candidate or control phage clones, the organs and tumors were removed and divided into two parts. One part was titered by ER2738, and another part was embedded in Optimal Cutting Temperature (OCT, Tissue-Tek, NL, USA). The OCT-embedded frozen tissues were sectioned at 5 microns and transferred to cold PBS buffer. Then, the sections were fixed with acetone-methanol (1:1), washed with PBS and immersed in blocking buffer (1% BSA in PBS) for 1 h. The blocked samples were then incubated with rat anti-mouse CD31 (BD Pharmingen, Mass., USA.), rabbit anti-rat Ab (Stressgen, Canada) and immersed in Rhodamine labeled goat anti-rabbit antibody (Jackson ImmunoResearch, Pa., USA.). The slides were further incubated with mouse anti-M13 mAb (Amersham Biosciences, Uppsala, Sweden), followed by incubation with FITC-labeled goat anti-mouse antibody (Jackson ImmunoResearch) and immersed with Hoechst 33258 (Molecular probe, OR, USA). Finally the slides were washed and mounted with mounting medium (Vector, Calif., USA).

We also used the FITC-labeled candidate peptides and control peptide in place of the phages. In a peptide binding assay, FITC-labeled peptides were injected in tumor xenograft mice through the tail vein. After perfusion, the tissues were removed and treated as above. Then the slides were examined under a Leica Universal microscope. The images were merged by SimplePCI (C-IMAGING, PA, USA) software.

PC5-52 showed homing ability in tumor mass, exhibiting from 8.0 to 135 fold higher concentration in tumor mass than in other organs, including brain, lung, and heart (FIG. 2A), while control helper phage revealed no such homing ability (FIG. 2B).

The tumor homing ability of PC5-52 was also proved by a ligand competition experiment. Candidate peptides SVSVG-MKPSPRP (SP5-52) and control peptide (RLLDTNR-PLLPY) [SEQ ID NO: 20] were synthesized and purified by reverse-phase high-performance liquid chromatography to >95% purity by Invitrogene, Inc. (CA, USA). Conjugation of these peptides with FITC or biotin was performed by adding FITC or biotin to the peptide $NH_2$ terminus by the same company. A ligand competition experiment showed that co-injection of synthetic SP5-52 peptide with PC5-52 phage particles inhibited recovery of PC5-52 from tumor tissues (FIG. 2B). 100 μg of SP5-52 inhibited 97% of PC5-52 homing to NSCLC tumor mass. Similar results showed that IVO-2 (which displays a peptide with the same amino acid sequence as the peptide displayed by PC5-52) also homes to tumor tissues of oral cancer xenografts (FIG. 2C). IVO-2 showed homing ability in tumor mass with 12 to 121 fold higher concentration in tumors than in other organs, including brain, lung, and heart (FIG. 2C). The tumor homing ability of IVO-2 could be inhibited by SP5-52. Coinjection of 100 μg of SP5-52 inhibited 95.9% of IVO-2 homing to oral cancer xenografts (FIG. 2D). Control peptide could not inhibit IVO-2 homing to tumor tissue (FIG. 2D). After 24 h injection of PC5-52, we also found that the phages accumulated 10 fold more in tumor tissue than in control tissues.

Example 3

Localization of PC5-52 and SP5-52

To investigate the homing specificity of PC5-52, we used an immunofluorescent assay to localize the binding activity of the phage after perfusion. Human lung adenocarcinoma frozen sections were prepared as above. The slides were incubated in blocking buffer for 30 min, and then treated with 3% hydrogen peroxide plus 0.1% $NaN_3$ in methanol to block endogenous peroxidase activity, and incubated with biotin-labeled peptide. The slides were subjected to routine immunohistochemical staining.

The results showed that phage particles reacted with xenograft tumor sections of lung cancer but not with normal lung tissues (FIG. 3A). However, the phage did not localize to cancer cells. Tumor masses appear in panel (a), while normal lung appears in panel (c). Panels (b) and (d) are counter stained for nuclear DNA with H33258, and correspond to panels (a) and (c), respectively. When we used frozen sections from tumor tissues that were incubated with anti-M13 mAb (green) and mouse endothelial cell marker CD31 (red), we found that PC5-52 colocalized with CD31 in the tumor vasculature of xenograft tumor tissues (FIG. 3B). The phage was not found in normal heart (FIG. 3B), lung and brain vessels. Colocalization of anti-phage immunofluorescence with anti-CD31 on tumor vasculature endothelia after phage injection appears in panels (i-k). Control phage cannot bind tumor vessels (a), while PC5-52 cannot recognize normal heart (e). Anti-CD31 is shown in heart vessels (f and g) and xenograft tumor vessels (b, c, j, and k). Nuclear staining appears in (d, h, and l.)

To further investigate phage-displayed peptide homing to tumor vasculature, we used a FITC-labeled SP5-52 peptide in place of PC5-52 phage for peptide-homing studies. We found that the FITC-labeled SP5-52 peptides were also colocalized with mouse CD31 marker in tumor vasculature of lung cancer xenografts (FIG. 3C i-i). This peptide did not react with heart vessels (FIG. 3C e-h). FITC-labeled control peptide could not recognize the tumor vasculature (FIG. 3C a-d). Rhodamine-anti-CD31 is shown in the human lung cancer xenografts (b, and j) and normal heart (f). Nuclear staining with H33253 appears in (d, h, and l). (Bar, 20 μm).

Example 4

Binding of PC5-52 to Multiple Cancer Xenografts, and Investigation of the PSP Motif We isolated tumor homing phage PC5-52 from lung and oral cancer xenografts by in vivo phage display. These results indicate that the target of SP5-52 may be expressed in the vasculature of solid tumors. To test this hypothesis, we examined the homing ability of PC5-52 on other six different types of human cancers including human lung (H460), colon (HCT116), breast (BT483), prostate (PC3), liver (Mahlavu), and pancreatic (PaCa) cancer xenografts. SCID mice were injected i.v. with PC5-52. After 8 min, the free phages were washed out by perfusion with PBS buffer, and xenograft tumor masses were removed for determination of phage titer. PC5-52 targeted to tumor tissues but not normal organs like brain, lung and heart in all of these human cancer xenografts (FIG. 4). Control phage without this targeting ligand had no such homing ability.

From in vivo phage display, we found that the peptides displayed by three clones (PC5-5, PC5-52 and PC5-54) have a consensus motif of Proline (P)-Serine (S)-Proline (P) (Table 1). We proposed that these three amino acid residues play a role in homing to tumor tissues. To test this hypothesis, we changed these three amino acid residues in SP5-52 (SVSVG-MKPSPRP) to GGG in mutant peptide MP5-52 (SVSVG-MKGGGRP) (SEQ ID NO: 20). Tumor homing phage PC5-52 could target to CL1-5-derived tumors in the in vivo homing assay (FIG. 4B). The tumor homing ability of PC5-52 was inhibited markedly by SP5-52, but not by mutant peptide in MP5-52 (FIG. 4B).

Example 5

PC5-52 Reacts With Stimulated HUVECs and SP5-52 Binds to Human Lung Cancer Biopsy Specimens To further identify whether this phage has affinity for human neovasculature endothelia, we applied the PC5-52 phage particles to VEGF-stimulated human vascular endothelial cells (HUVECs). HUVECs were plated and grown to about 80% confluence on cover slips. The cells were pre-treated with VEGF (B&D Systems, Minn., USA) and bFGF (PEPROTECH, Landon, UK) for 48 h. The VEGF-stimulated HUVECs were washed with serum-free M199 and incubated in blocking buffer (serum-free M199 plus 3% BSA) for 30 min at 4° C. Then the cover slips were incubated with phages at 4° C. for 1 h, washed and fixed with 3% formaldehyde for 10 min. The cover slips were then incubated with mouse anti-M13 mAb (Amersham Biosciences) for 1 h, followed by incubation with FITC-labeled anti-mouse antibody (Jackson ImmunoResearch) and then immersed with Hoechst 33258. The cover slips were finally washed and mounted with mounting medium.

The results revealed that PC5-52 bound to VEGF-stimulated HUVECs (FIG. 5A, a). The binding of PC5-52 was not observed in HUVECs without VEGF stimulation (FIG. 5A, b). The control phage without this peptide revealed no binding activity (FIG. 5A, c). Furthermore, biotin-labeled SP5-52 peptide could bind to tumor vessels of human lung cancer biopsy specimens but not to non-tumor vessels of control lung (FIG. 5B). These data indicate that SP5-52 recognized unknown receptor on human angiogenic endothelial cells and tumor neovasculature.

To determine if the binding of phage to tumor vessels was mediated through the displayed peptides, FITC-labeled peptide is used in place of the phage in a HUVECs binding study. The HUVECs on cover slips are incubated with FITC-labeled peptide or control peptide for 2 h. Then, the cover slips are washed and immersed with Hoechst 33258, and then washed and mounting with mounting medium, and examined under a Leica Universal microscope.

Example 6

Preparation of Peptide-Liposome Containing Doxorubicin and Treatment of an Animal Model To determine whether the tumor vessel-homing peptide, SP5-52, could be used to improve the therapeutic efficacy of cancer chemotherapeutics, we coupled SP5-52 to liposomes containing doxorubicin (SP5-52-Lipo-Dox) and treated mice bearing xenografts with the liposomes.

The procedures for preparation of liposome containing doxorubicin were adapted from the methods published in previous reports (Lee et al., 2004; Tseng et al., 1999). Briefly, L-peptide was coupled to NHS-PEG-DSPE N-hydroxysuccinimido-carboxyl-polyethylene glycol (PEG; average molecular weight, 3000)-derived distearoylphosphatidylethanolamine (NOF Corporation, Tokyo, Japan) at a 1:1.5 molar ratio. This coupling was done using the unique free amine group in the N terminus of the peptide to produce peptidyl-PEG-DSPE. The reaction was completed and confirmed by quantitation of the remaining amino groups. The amino groups were measured with TNBS (Trinitrobenzenesulfonate) reagent (AFSA., 1966).

Liposomes composed of DSPC (distearoylphosphatidylcholine), cholesterol, PEG-DSPE were hydrated at 55° C. in ammonium sulfate solution (250 mM $(NH_4)_2SO_4$, pH=5.0, 530 mOs) and extruded through polycarbonate membrane filters (Costar, Cambridge, Mass., USA) of 0.1 μm and 0.05 μm pore size using high-pressure extrusion equipment (Lipex Biomembranes, Vancouver, BC, Canada) at 60° C., and doxorubicin was encapsulated in the liposomes by a remote loading method at a concentration of 1 mg doxorubicin per 10 μmol phospholipid. The final concentration of liposomes was determined by phosphate assay. After adding 1 ml acidic isopropanol (81 mM HCl) to 0.2 ml diluted drug-loaded liposomes, the amount of doxorubicin trapped inside the liposomes was determined with a spectrofluorometer (Hitachi F-4500, Hitachi, Ltd, Tokyo, Japan) using 470 nm as excitation wavelength and 582 nm as emission wavelength. Vesicle sizes were measured by dynamic laser scattering with a submicron particle analyzer (model N4 plus; Coulter Electronics, Hialeah, Fla., USA). After preparation, the liposomes contained 110 μg to 130 μg doxorubicin per μmol phospholipid and had a particle size ranging from 65 nm to 75 nm in diameter. The same method was used to prepare a control peptide coupled to NHS-PEG-DSPE for comparison. Peptidyl-PEG-DSPE was transferred to pre-formed liposomes after co-incubation at temperature above the transition temperature of lipid bilayer (Zalipsky et al., 1997). There were 300-500 peptide molecules per liposome, computed as described previously (Kirpotin et al., 1997).

Human lung (CL1-5) and oral (SAS) cancer xenografts were established in SCID mice. Mice 4-6 weeks of age were injected s.c. into the dorsolateral flank with human cancer cells. Mice with size-matched tumors (tumor sizes about 100 mm$^3$) were randomly assigned to different treatment groups and treated with multiple doses (1 mg/kg, twice a week) of SP5-52-Lipo-Dox, and Lipo-Dox through the tail vein. The control group was administered with PBS i.v. at the same volume and schedule as SP5-52-Lipo-Dox. Mouse body weight and tumor size were measured twice a week by a caliper. The tumor volumes were calculated using the equation: volume=length×(width)$^2$×0.52. The differences in mean tumor volume were evaluated by ANOVA.

SCID mice bearing CL1-5-derived tumors (tumor size about 100 mm$^3$) were randomly separated into three groups and treated with SP5-52-Lipo-Dox, Lipo-Dox or PBS through i.v. at a total doxorubicin dose of 7 mg/kg (1 mg/kg, twice a week). The SP5-52-peptide-Lipo-Dox treated mice showed significantly smaller tumor size than that of Lipo-Dox and PBS treated cases ($P<0.01$) (FIG. 6A). The tumor size of mice in the Lipo-Dox group gradually increased to 1.9-fold larger than those in the SP5-52-Lipo-Dox group by day 28. The tumor size in mice of the control PBS group was 4.1-fold larger than those of the SP5-52-Lipo-Dox group. To further characterize the therapeutic efficacy of the targeting liposomes, we compared the animal survival rate after treatment with SP5-52-Lipo-Dox, Lipo-Dox or PBS separately. All animals (n=6) died in the group of PBS and Lipo-Dox treatment (0% survival rate), only two animals were died in the group of SP5-52-Lipo-Dox treatment (66.7% survival rate) when the experiment was finished at day 81 (FIG. 6B). We also found the tumor vessels were markedly decreased and damaged on SP5-52-Lipo-Dox treated mice (FIG. 6C).

To test whether SP5-52 could increase the therapeutic efficacy for oral cancer, we also developed ligand-targeted therapy for this cancer in an animal model. Similar results were found in SCID mice bearing SAS-derived oral cancer treated with a targeting liposome. Treatments with SP5-52-Lipo-Dox, Lipo-Dox, or PBS were administered i.v. at total doxorubicin dose of 7 mg/kg (7 times, 1 mg/kg twice a week). The SP5-52-peptide-Lipo-Dox treated mice showed significantly smaller tumor size than that of Lipo-Dox and PBS treated mice (P<0.05) (FIG. 6D). The tumor size in mice of the Lipo-Dox group gradually increased to 3.6-fold larger than those of the SP5-52-Lipo-Dox group on day 24.5. Mice in the control PBS group were found to have tumor size 7.1-fold larger than those in SP5-52-Lipo-Dox group (FIG. 6D). Furthermore, all animals (n=6) died in the group of PBS treatment (0% survival rate), four animals died in the group of Lipo-Dox treatment (33.3% survival rate), while the SP5-52-Lipo-Dox treated group all survived (100% survival rate) when the experiment was finished at day 60 (FIG. 6E). We repeated this experiment again and the results further confirmed that SP5-52-Lipo-Dox was more effective than Lipo-Dox in treating oral cancer xenografts. The tumor size in mice treated with Lipo-Dox gradually increased to 3.2-fold larger than those of the SP5-52-Lipo-Dox group. The tumor size in mice treated with control PBS was found to be 5.9-fold larger than those in the SP5-52-Lipo-Dox group. These results demonstrate that conjugation of Lipo-Dox with targeting ligand SP5-52 enhances the ability of drugs to inhibit solid tumor xenografts, including human lung and oral cancer xenografts in SCID mice.

TABLE 1

Alignment of phage-displayed peptide sequences selected from lung cancer cell xenografts

| Phage clone | Phage-displayed peptide sequence[a] | |
|---|---|---|
| PC5-52 | SVSVGMKPSPRP | (SEQ ID NO: 2) |
| PC5-54 | WPLHTSVYPPSP | (SEQ ID NO: 4) |
| PC5-5 | NTLPPFSPPSPP | (SEQ ID NO: 6) |
| PC5-10 | SFPDSNIAPSSP | (SEQ ID NO: 8) |
| PC5-8 | QHAPSNSKSVLT | (SEQ ID NO: 10) |
| PC5-60 | NSHQALWSPAQ | (SEQ ID NO: 12) |
| PC5-58 | SPMFTMIQGDAQ | (SEQ ID NO: 14) |
| PC5-53 | SPLLSTRAVQLS | (SEQ ID NO: 16) |
| PC5-4 | STLPPPLRFANV | (SEQ ID NO: 18) |

[a]Phage-displayed consensus amino acids are shown in boldface.

The invention claimed is:

1. A peptide-conjugate comprising,
   (i) a peptide that binds to VEGF-stimulated or to tumor vasculature with a higher affinity than to normal vasculature, wherein the peptide comprises:
       (a) SEQ ID NO: 4 or SEQ ID NO: 6, or
       (b) a variant of SEQ ID NO: 2, SEQ ID NO: 4, or SEQ ID NO: 6, wherein the variant comprises amino acids PSP, and wherein the variant is not SEQ ID NO: 2, and
   (ii) a conjugate chosen from a macromolecular carrier and one or more drugs, wherein the one or more drugs are chosen from doxorubicin, vinorelbine, a toxin, an anti-VEGF aptamer, and a radioactive molecule.

2. The peptide-conjugate of claim 1, wherein the peptide is encoded by a polynucleotide that hybridizes under stringent conditions to the complement of a polynucleotide chosen from SEQ ID NO: 1, SEQ ID NO: 3, and SEQ ID NO: 5, and wherein the peptide comprises amino acids PSP, wherein said stringent conditions comprise hybridization in 4× sodium chloride/sodium citrate (SSC) at about 65-70° C. or hybridization in 4×SSC plus 50% formamide at about 42-50° C.

3. The peptide-conjugate of claim 1, wherein the peptide comprises a variant of SEQ ID NO: 2 comprising PSP.

4. The peptide-conjugate of claim 3, wherein the peptide is encoded by a polynucleotide that hybridizes under stringent conditions to the complement of SEQ ID NO: 1, wherein said stringent conditions comprise hybridization in 4× sodium chloride/sodium citrate (SSC) at about 65-70° C. or hybridization in 4×SSC plus 50% formamide at about 42-50° C.

5. The peptide-conjugate of claim 3, wherein the peptide is encoded by a polynucleotide that hybridizes under stringent conditions to the complement of SEQ ID NO: 3 or SEQ ID NO: 5, wherein said stringent conditions comprise hybridization in 4× sodium chloride/sodium citrate (SSC) at about 65-70° C. or hybridization in 4×SSC plus 50% formamide at about 42-50° C.

6. The peptide-conjugate of claim 1, wherein the peptide is encoded by a polynucleotide chosen from SEQ ID NO: 3, and SEQ ID NO: 5.

7. The peptide-conjugate of claim 1, wherein the peptide comprises SEQ ID NO: 4.

8. The peptide conjugate of claim 1, wherein the peptide comprises a variant of SEQ ID NO: 4 comprising PSP.

9. The peptide-conjugate of claim 1, wherein the drug is doxorubicin.

10. The peptide-conjugate of claim 1, wherein the macromolecular carrier is a liposome.

11. The peptide-conjugate of claim 10, wherein the liposome is coated with polyethylene glycol.

12. The peptide-conjugate of claim 10, wherein the liposome comprises polyethylene-derivatized phosphatidylethanolamine or polyethylene-derivatized distearoylphosphatidylethanolamine.

13. The peptide-conjugate of claim 10, wherein the liposome comprises or one or more drugs chosen from doxorubicin, vinorelbine, an oligonucleotide, a toxin, an anti-VEGF aptamer, and a radioactive molecule.

14. The peptide-conjugate of claim 13, wherein the drug is doxorubicin.

15. The peptide-conjugate of claim 1, wherein the peptide binds to tumor vasculature with a higher affinity than normal vasculature.

16. The peptide-conjugate of claim 15, wherein the tumor vasculature is lung cancer vasculature or oral cancer vasculature.

17. The peptide-conjugate of claim 15, wherein the peptide binds to endothelial cells of the tumor vasculature.

18. The peptide-conjugate of claim 1, wherein the peptide binds to VEGF-stimulated vasculature with a higher affinity than normal vasculature.

19. A method of treating a subject suffering from a disease accompanied by neovascularization comprising administering to the subject an effective amount of the peptide of claim 1.

20. The method of claim 19, wherein the mammal is human.

21. The method of claim 19, wherein the disease is cancer, proliferative diabetic retinopathy, retinopathy of prematurity, or age-related macular degeneration.

22. The method of claim 21, wherein the cancer is lung cancer, colon cancer, breast cancer, prostate cancer, liver cancer, pancreatic cancer, or oral cancer.

* * * * *

UNITED STATES PATENT AND TRADEMARK OFFICE
CERTIFICATE OF CORRECTION

| | |
|---|---|
| PATENT NO. | : 8,088,887 B2 |
| APPLICATION NO. | : 11/783926 |
| DATED | : January 3, 2012 |
| INVENTOR(S) | : Han-Chung Wu et al. |

It is certified that error appears in the above-identified patent and that said Letters Patent is hereby corrected as shown below:

Column 33, line 2, "comprising," should read --comprising:--.

Column 34, line 14, "comprises or one or more drugs" should read --comprises one or more drugs--.

Signed and Sealed this
First Day of May, 2012

David J. Kappos
*Director of the United States Patent and Trademark Office*